United States Patent
Weiss et al.

(10) Patent No.: US 10,449,182 B2
(45) Date of Patent: Oct. 22, 2019

(54) SORAFENIB DERIVATIVES AS P21 INHIBITORS

(71) Applicant: The Regents of the University of California, Oakland, CA (US)

(72) Inventors: Robert H. Weiss, Vacaville, CA (US); Bruce D. Hammock, Davis, CA (US); Hiromi Inoue Wettersten, Sacramento, CA (US); Sung Hee Hwang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/408,280

(22) PCT Filed: Jun. 20, 2013

(86) PCT No.: PCT/US2013/046848
§ 371 (c)(1),
(2) Date: Dec. 15, 2014

(87) PCT Pub. No.: WO2014/007998
PCT Pub. Date: Jan. 9, 2014

(65) Prior Publication Data
US 2015/0132408 A1    May 14, 2015

Related U.S. Application Data

(60) Provisional application No. 61/668,903, filed on Jul. 6, 2012.

(51) Int. Cl.
| | |
|---|---|
| *A61K 31/44* | (2006.01) |
| *A61K 31/4439* | (2006.01) |
| *A61K 31/17* | (2006.01) |
| *A61K 31/192* | (2006.01) |
| *A61K 31/277* | (2006.01) |
| *A61P 35/02* | (2006.01) |
| *A61P 35/00* | (2006.01) |
| *A61K 31/4412* | (2006.01) |
| *A61K 45/06* | (2006.01) |
| *A61K 31/196* | (2006.01) |
| *A61K 31/675* | (2006.01) |
| *A61K 31/704* | (2006.01) |
| *A61K 33/24* | (2019.01) |

(52) U.S. Cl.
CPC .......... *A61K 31/4412* (2013.01); *A61K 31/17* (2013.01); *A61K 31/196* (2013.01); *A61K 31/277* (2013.01); *A61K 31/44* (2013.01); *A61K 31/4439* (2013.01); *A61K 31/675* (2013.01); *A61K 31/704* (2013.01); *A61K 33/24* (2013.01); *A61K 45/06* (2013.01)

(58) Field of Classification Search
CPC ... C07C 275/38; C07C 275/30; C07C 275/34; C07C 275/26; C07C 2101/14; C07D 213/64; C07D 213/79; C07D 213/81; C07D 213/643; C07D 213/65; C07D 213/68; C07D 401/06; A61K 31/44; A61K 31/4439; A61K 31/17; A61K 31/192; A61K 31/277
See application file for complete search history.

(56) References Cited

U.S. PATENT DOCUMENTS

| | | | |
|---|---|---|---|
| 9,029,401 B2 * | 5/2015 | Hammock | C07D 213/64 435/15 |
| 2006/0063785 A1 | 3/2006 | Wang et al. | |
| 2009/0012091 A1 | 1/2009 | Yu | |
| 2009/0023731 A1 | 1/2009 | Gless, Jr. et al. | |
| 2011/0098322 A1 | 4/2011 | Sanborn et al. | |
| 2014/0088156 A1 * | 3/2014 | Hammock | C07D 213/64 514/343 |

FOREIGN PATENT DOCUMENTS

WO    2012/112570 A1    8/2012

OTHER PUBLICATIONS

Chang et al. PNAS 2000, 97 (8), 4291-4296.*
Kumar et al. Nature Reviews Cancer 2006, 6, 459-471.*
Scatizzi et al. Eur. J. Immunol. 2009, 39 (3), 820-825.*
Taglieri et al. Cell Signal 2014, 26 (9), 2060-2069.*
Weiss et al. Journal of Urology 2007, 177, 63-69.*
Nanus et al. Cancer 2004, 101, 7, 1545-1551.*
Liu et al. Mol. Cancer Ther. 2009, 8(8), 2193-2203.*
Grivennikov et al. Cell 2010, 140, 883-899.*
Zhang et al. J. Natl. Cancer Inst. 2008, 100, 184-198.*
Inoue, et al., "Sorafenib attenuates p21 in kidney cancer cells and augments cell death in combination with DNA-damaging chemotherapy," *Cancer Biology & Therapy*, vol. 12(9), pp. 827-836 (2011).
International Search Report and Written Opinion for International Application No. PCT/US2013/046848 dated Nov. 22, 2013, 9 pages.

* cited by examiner

*Primary Examiner* — Irina Neagu
(74) *Attorney, Agent, or Firm* — Mintz, Levin, Cohn, Ferris, Glovsky and Popeo, P.C.

(57) ABSTRACT

The present invention provides sorafenib analogs for use in a method of treating a disease mediated by p21, said method comprising administering to a subject in need thereof a therapeutically effective amount of a compound of formula I. The present invention also provides methods of inhibiting p21 in a cell comprising contacting the cell with an effective amount of a compound of formula I.

6 Claims, 9 Drawing Sheets

Non-Small Cell Lung Cancer

Melanoma

Prostate Cancer

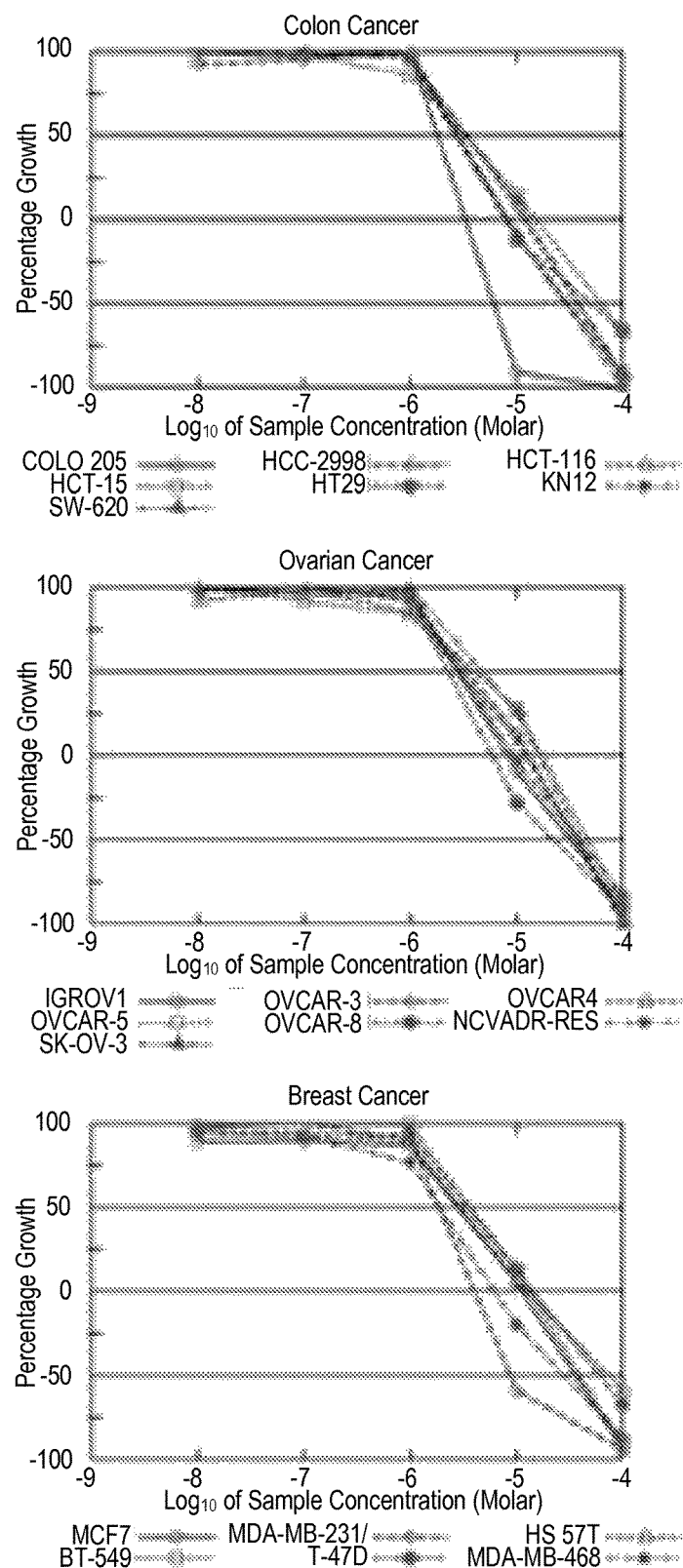

| | IC$_{50}$ (nM) | | VEGFR2 inhibition at 10 μM (%) |
| --- | --- | --- | --- |
| | C-Raf | B-Raf$^{V600E}$ | |
| Sorafenib | 45 ± 5 | 13 ± 2 | 100 |
| UC2288 | > 10000 | > 10000 | 0 |

SORAFENIB DERIVATIVES AS P21 INHIBITORS

CROSS-REFERENCES TO RELATED APPLICATIONS

This application is the U.S. National Stage Entry under 35 U.S.C. § 371 of International Application No. PCT/US2013/046848, filed Jun. 20, 2013, which claims priority to U.S. Provisional Application No. 61/668,903, filed Jul. 6, 2012, which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. CA135401, DK082690, ES002710 and ES004699, awarded by the National Institutes of Health. The Government has certain rights in this invention.

BACKGROUND OF THE INVENTION

Kidney cancer (or renal cell carcinoma; RCC) is responsible for 13,000 deaths annually in the US. The disease is frequently asymptomatic, and a third of cases are diagnosed when the disease is already metastatic, at which time it has 95% mortality (Weiss R H, Lin P-Y. Kidney Int 2006; 69(2):224-232). Conventional treatment of RCC has been based on surgical approaches and the administration of the immunomodulating medications interferon and interleukin-2 (reviewed in Weiss R H, Lin P-Y. Kidney Int 2006; 69(2):224-232). These drugs, their combinations with cytotoxic "standard" treatments such as gemcitabine and 5-FU (Stadler W M, Huo D, George C, Yang X, Ryan C W, Karrison T et al. J Urol 2003; 170(4 Pt 1):1141-1145), other cytostatic chemotherapy agents alone and in combination, as well as hormonal manipulation, have all shown no benefit to survival and are thus not generally utilized (reviewed in De Mulder P H, van Herpen C M, Mulders P A. Ann Oncol 2004; 15 Suppl 4:iv319-iv328). Novel targeted therapies are just beginning to emerge, with the most promising being the kinase inhibitors sorafenib and sunitinib (reviewed in Tuma R S. J Natl Cancer Inst 2004; 96(17):1270-1271). However, new pharmacological approaches which would cause standard therapies to be effective in this disease would be a welcome addition to the limited available armamentarium.

p21 is a member of the cip/kip family of cyclin kinase "inhibitors," but this protein also possesses a variety of properties relating to apoptosis (Matsushita H, Morishita R, Kida I, Aoki M, Hayashi S, Tomita N et al. Hypertension 1998; 31:493-498; Asada M, Yamada T, Ichijo H, Delia D, Miyazono K, Fukumuro K et al. EMBO J 1999; 18(5):1223-1234; Tian H, Wittmack E K, Jorgensen T J. Cancer Res 2000 Feb. 1; 60 (3):679-84 2000; 60:679-684; Fan Y, Borowsky A D, Weiss R H. Mol Cancer Ther 2003; 2(8): 773-782) as well as cell proliferation (Weiss R H, Joo A. Randour C. J Biol Chem 2000; 275:10285-10290; Kavurma M K, Khachigian L M. J Biol Chem 2003: 278:32537-32543; Dong Y. Chi S L, Borowsky A D, Fan Y, Weiss R H. Cell Signal 2003; 16(2):263-269). The initial descriptions of p21 focused on its location in the tumor suppressor pathway downstream of p53 (el-Deiry W S, Tokino T, Velculescu V E, Levy D B, Parsons R Trent J M et al. Cell 1993; 75:817-825), its function as an inhibitor of $G_1$ cyclin kinases (Xiong Y, Hannon G J, Zhang H, Casso D, Kobayashi R, Beach D. Nature 1993; 366(6456):701-704; Harper J W, Adami G R, Wei N, Keyomarsi K, Elledge S J. Cell 1993; 75(4):805-816), and its role in differentiation (Sherr C J, Roberts J M. Genes and Dev 1999; 13:1501-1512). However, more recent investigations have shown that p21 also plays roles in allowing cell cycle transit as well as preventing apoptosis (Fan Y P, Weiss R H. J Am Soc Nephrol 2004; 15(3):575-584; Liu X F, Xia Y F, Li M Z, Wang H M, He Y X, Zheng M L et al. Cell Biol Int 2006; 30(3):283-287; Sohn D, Essmann F, Schulze-Osthoff K, Janicke R U. Cancer Res 2006: 66(23):11254-11262; Park S H, Park J Y, Weiss R H. J Urol 2008; 180(1):352-360); since programmed cell death is the ultimate mechanism by which cancer chemotherapeutics exert their salutary effects on tumor cells, this property of p21 has considerable untapped potential to be of fundamental importance in the therapy of human cancer.

For many cancers, treatment with DNA damaging agents, at doses required for efficacy, are associated with unacceptable adverse effects as well as inadequate cure rates. Kidney cancer is notoriously chemotherapy as well as "conventional" immunotherapy resistant, although recent work with kinase inhibitors has shown promise for late-stage disease. A possible reason for chemotherapy resistance is failure of these agents, when used alone, to cause cancer cell apoptosis, since inactivation of apoptosis is essential for cancer development (Brown J M, Attardi L D. Nat Rev Cancer 2005; 5(3):231-237; Evan G I, Vousden K H. Nature 2001; 411 (6835):342-348).

In breast cancer, increased cytosolic p21 or higher (total) p21 expression by immunostaining have been linked to poorer prognosis (Winters Z E, Leek R D. Bradburn M J, Norbury C J, Harris A L. Breast Cancer Res 2003; 5(6): 242-249), and efforts to attenuate p21 in vitro in breast cancer, and in vivo in breast, colon and esophageal cancers, have led to salutary effects on tumors cells. In kidney cancer, p21 has been shown to have prognostic value in the clear cell variety which is a function of whether patients have localized or metastatic disease at diagnosis (Weiss R H, Borowsky A D, Seligson D, Lin P Y. Dillard-Telm L, Belldegrun A S et al. J Urol 2007; 177(1):63-68). The likelihood that p21 is preventing cells from undergoing apoptosis and thereby allowing their escape from chemotherapy is supported by the finding that antisense oligodeoxynucleotides in vitro cause kidney cancer cells to be sensitized to DNA-damaging therapy, consistent with the anti-apoptotic effect of p21 observed in other cell lines (Asada M. Yamada T, Ichijo H, Delia D, Miyazono K. Fukumuro K et al. EMBO J 1999; 18(5):1223-1234).

p21 inhibitors have been reported previously (WO 10/039668), and sorafenib has been reported as a potent and stable p21 inhibitor (Inoue et al. (2011) Cancer Biol. Ther. 12(9):827-836). However, there still exists a need for compounds possessing similar or increased activity, with improved kinase selectivity. Surprisingly, the present invention provides compounds and compositions that meet this and other needs.

BRIEF SUMMARY OF THE INVENTION

In one embodiment, the present invention provides a method of treating a disease mediated by p21, the method including administering to a subject in need thereof a therapeutically effective amount of a compound of Formula I:

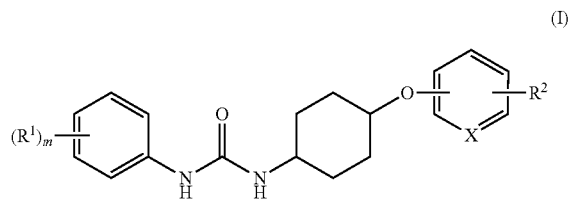

(I)

wherein $R^1$ is halogen, $C_{1-6}$ haloalkyl or $C_{1-6}$ haloalkoxy; $R^2$ is —CN, $C_{1-6}$ haloalkyl, $C_{1-6}$ haloalkoxy, —C(O)OR$^{2a}$ or —C(O)NR$^{2a}$R$^{2b}$; R$^{2a}$ and R$^{2b}$ are each independently H, $C_{1-6}$ alkyl or $C_{3-8}$ cycloalkyl, or are taken together to form a 5- or 6-membered heterocycloalkyl ring; X is —CH— or —N—; and the subscript m is an integer from 1 to 3; such that when X is —CH—, $R^2$ is —C(O)OH, and subscript m is 1, then $R^1$ is halogen or $C_{1-6}$ haloalkyl. The present invention also includes salts and isomers of the compounds of Formula 1.

In another embodiment, the present invention provides a method of inhibiting p21, the method including contacting p21 with a compound of Formula I:

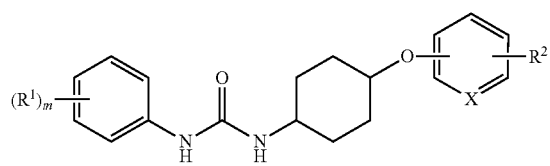

(I)

as defined above, in an amount sufficient to inhibit p21, thereby inhibiting p21.

In a further embodiment, the present invention provides a method of inhibiting p21, the method including contacting p21 with a compound, wherein the compound is:

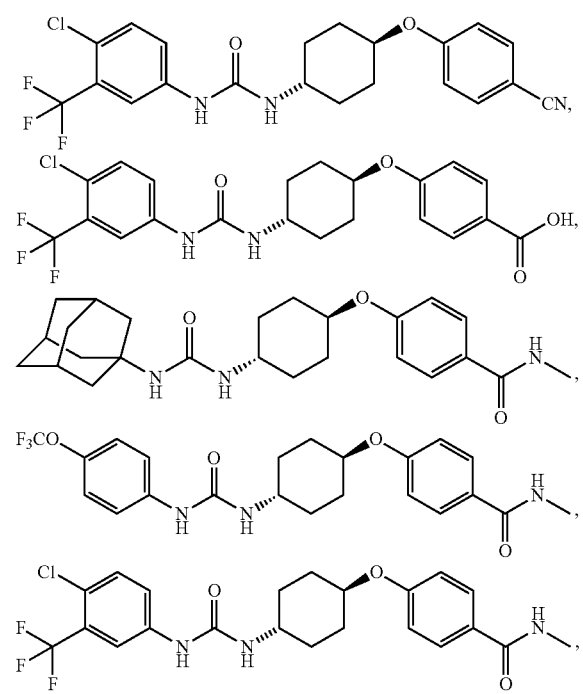

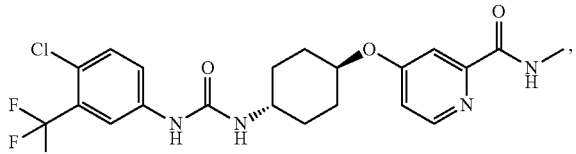

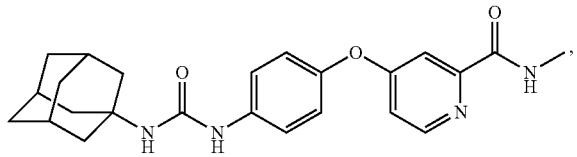

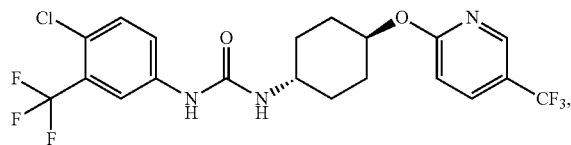

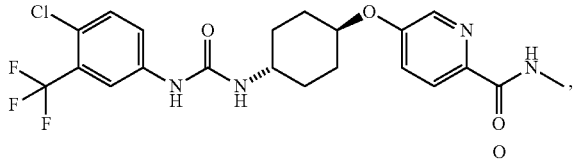

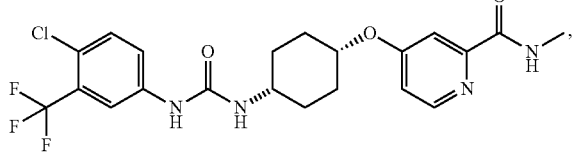

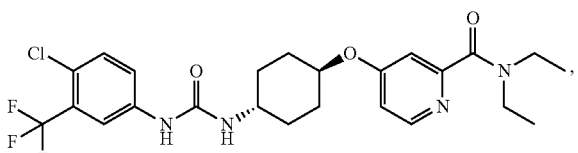

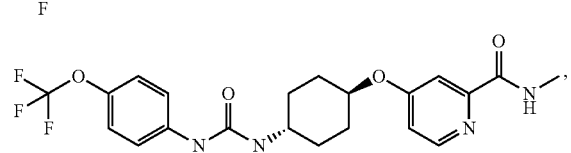

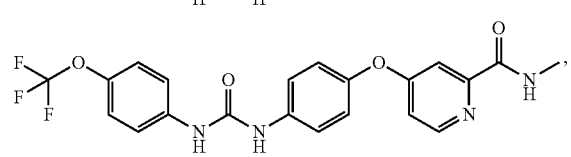

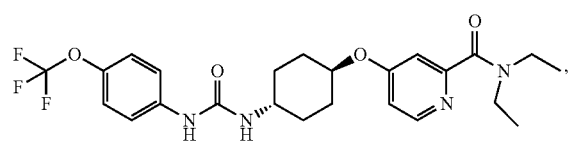

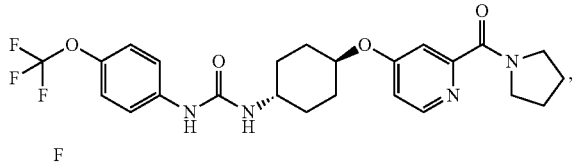

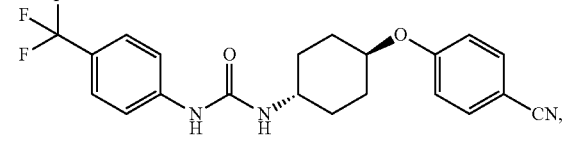

-continued

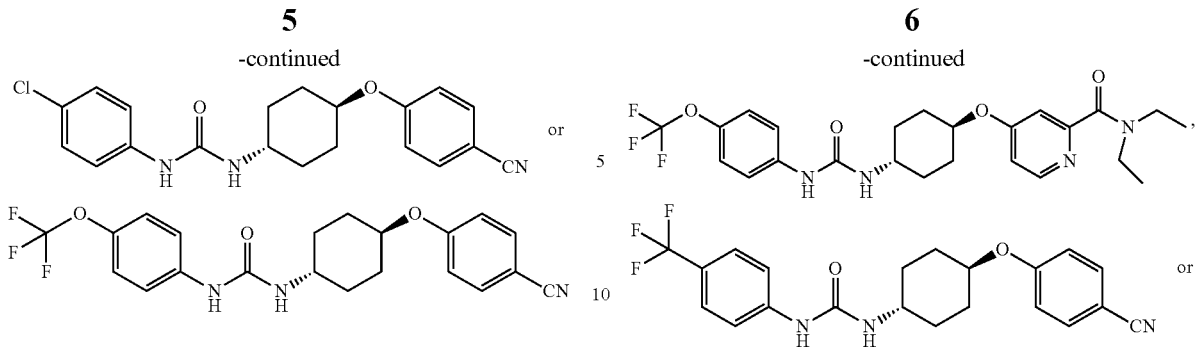

in an amount sufficient to inhibit p21, thereby inhibiting p21.

In yet another embodiment, the present invention provides a method of inhibiting p21, the method including contacting p21 with a compound, wherein the compound is:

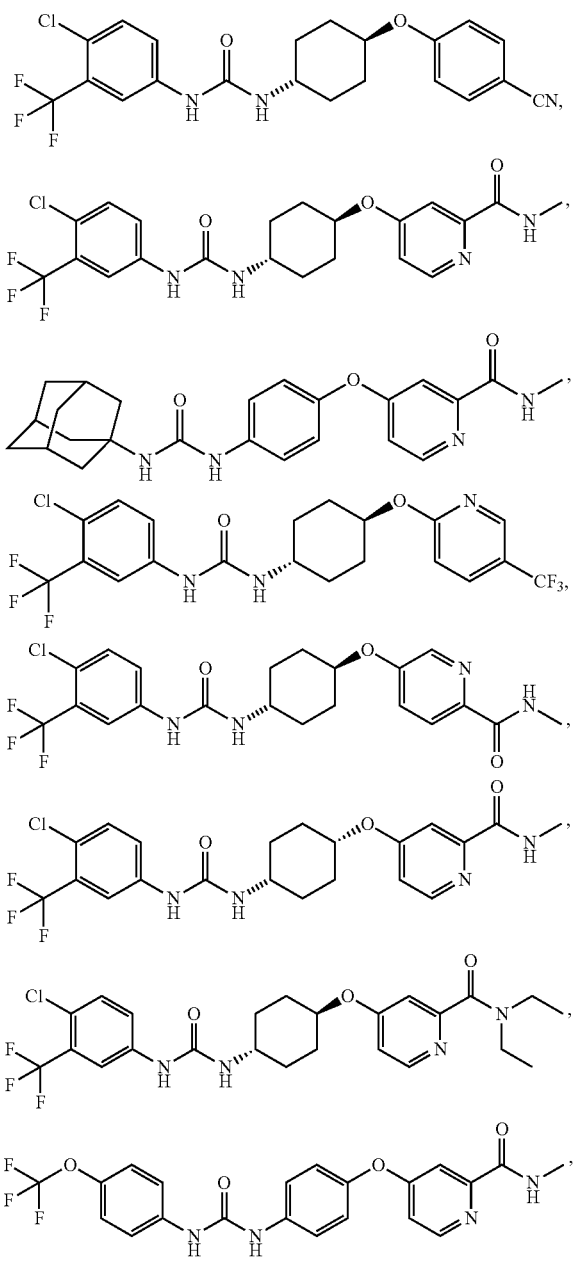

BRIEF DESCRIPTION OF THE DRAWINGS

FIGS. 4A, 4B & 4C. Compound 2288 inhibits cancer cell growth. TCA assay was conducted in the NCI60 cell lines treated with Compound 2288 as described in the Materials and Methods. Compound 2288 inhibited various cancer cell growth.

DETAILED DESCRIPTION OF THE INVENTION

I. General

Figure 1A:
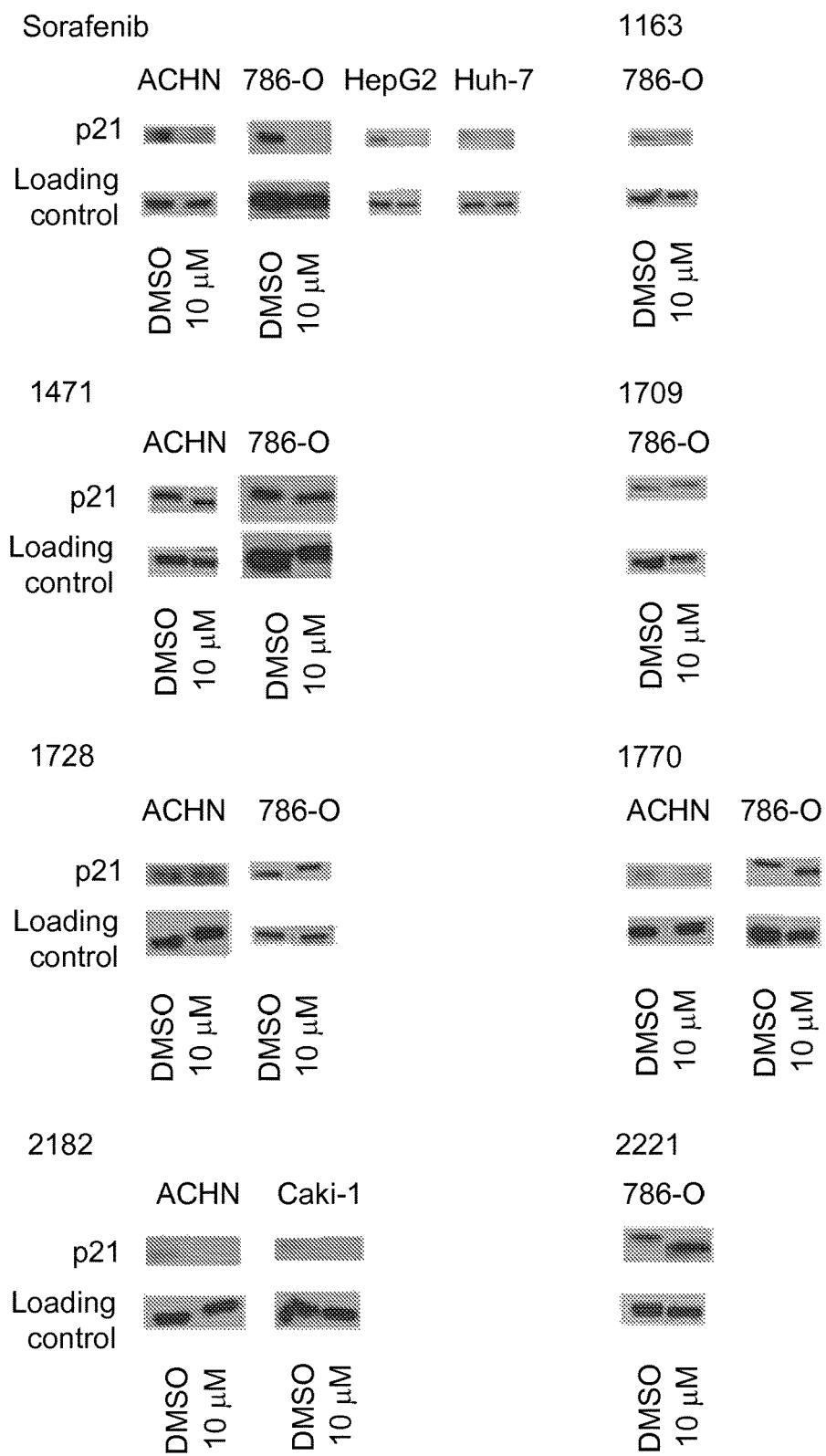
FIGS. 1a, 1b and 1c show renal cell cancer (RCC) cells (ACHN, Caki-1 or 786-O), hepatocellular carcinoma (HCC) cells (HepG2 or Huh-7) and ovarian cancer cells (Hey) grown to confluence in 10% serum-containing media and treated with DMSO or the indicated compounds (sorafenib, 1163, 1471, 1709, 1728, 1771, 2182, 2221, 2225, 2227, 2253, 2278, 2287, 2288, 2316, 2319, 2574, 2575, 2576, 2577, 2578, 2579, 2580 and 2581) at the indicated concentrations for 24 hours. Cells were harvested and immunoblotted with p21 antibodies. β-Actin or glyceraldehyde-3-phosphate dehydrogenase (GAPDH) was used as a loading control.
Figure 1B:
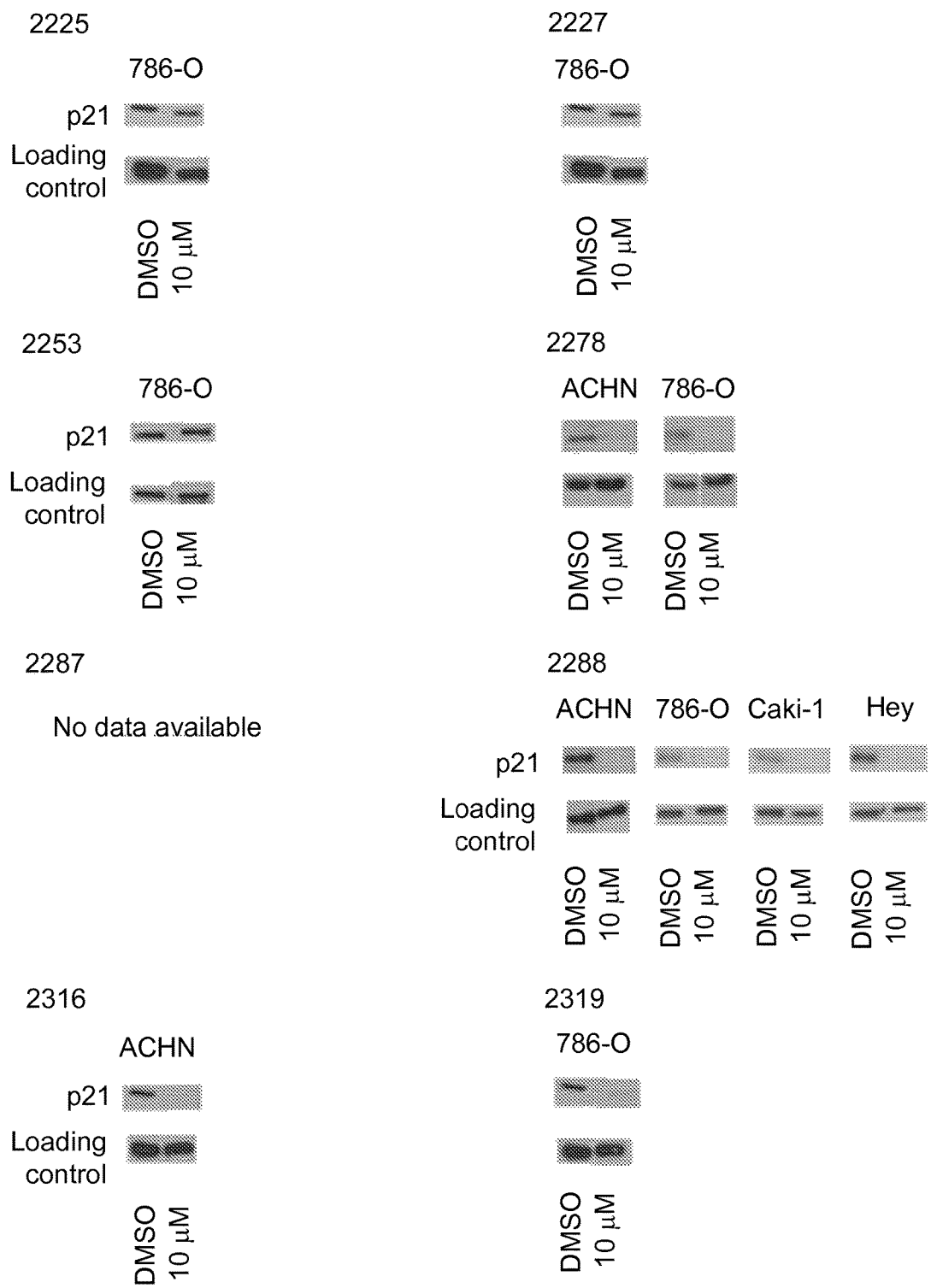
Figure 1C:
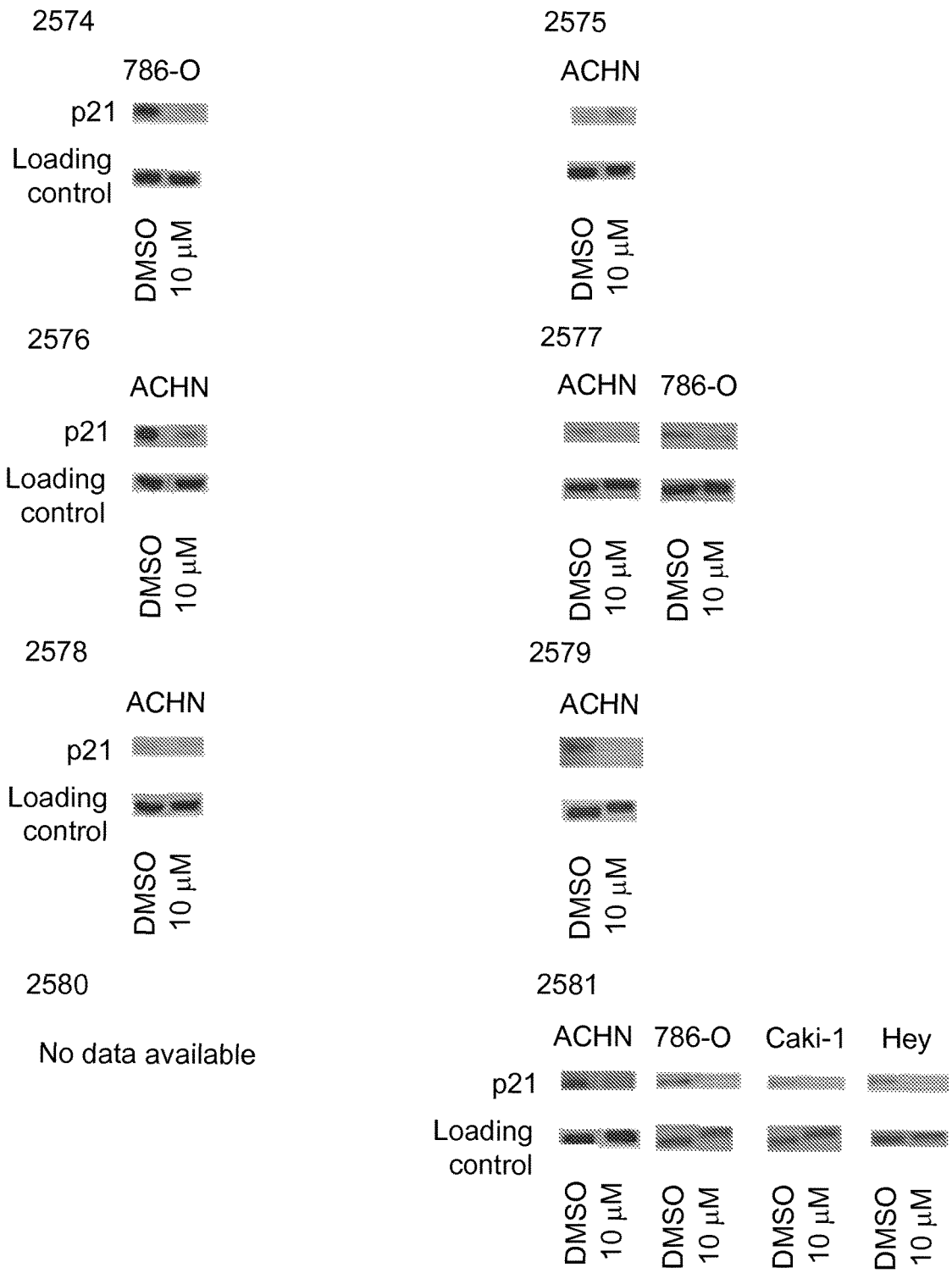
Figure 2:
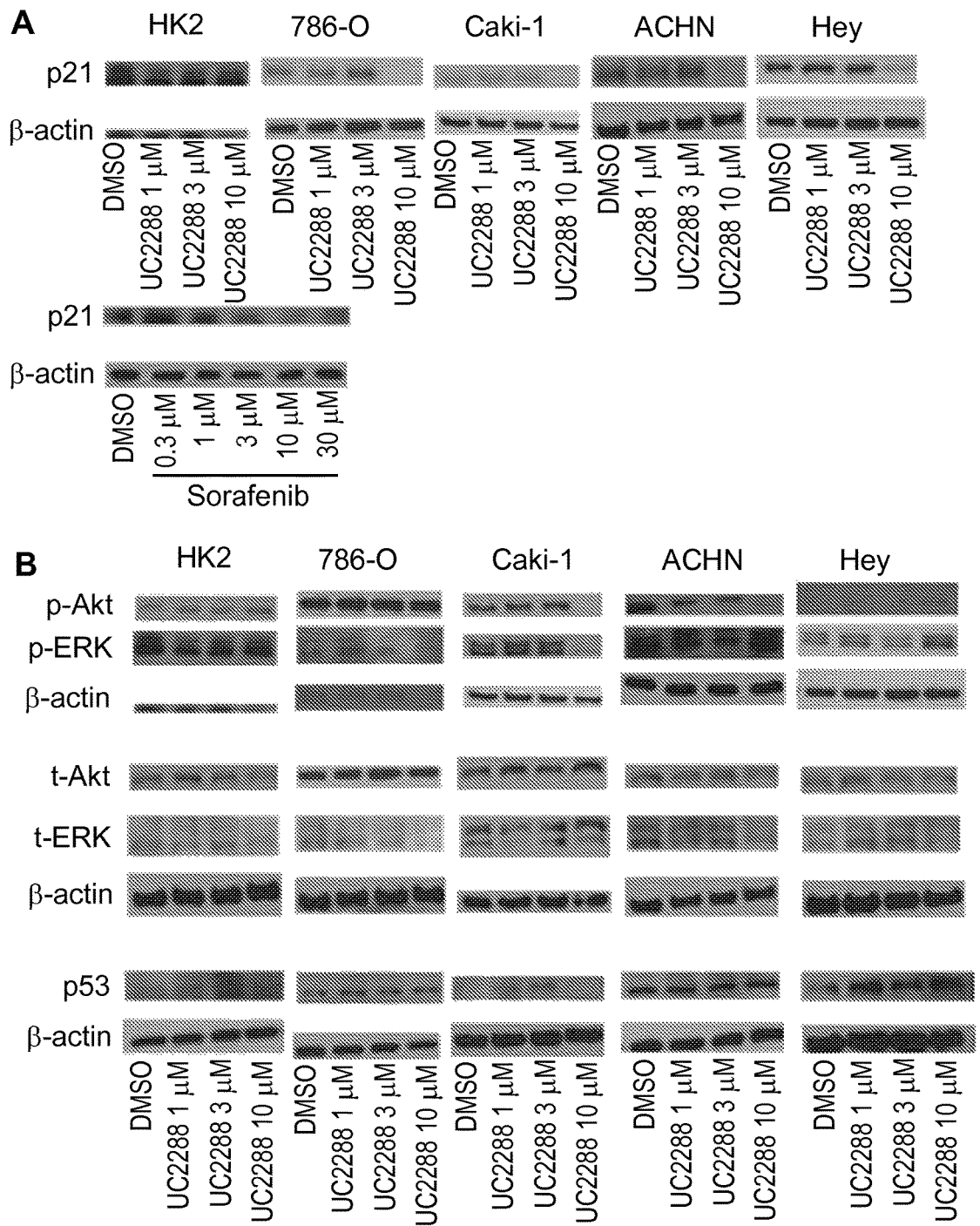
FIG. 2. Compound 2288 consistently decreases p21 protein level, but not levels of other proteins. Cancer cells and those derived from a normal kidney [HK2 (normal kidney), 786-O (RCC), Caki-1 (RCC), ACHN (RCC) and HE Y (ovarian cancer)] were grown to confluence in 10% serum-containing media and treated with either Compound 2288, sorafenib, or vehicle (DMSO) at the concentrations indicated for 24 h. The cells were harvested and immunoblotted with the antibodies indicated. (A) p21 and (B) p-Akt, p-ERK, t-Akt, t-ERK and p53 proteins are shown. β-actin is a loading control for each membrane. The experiment shown is representative of at least 3 separate experiments.
Figure 3:
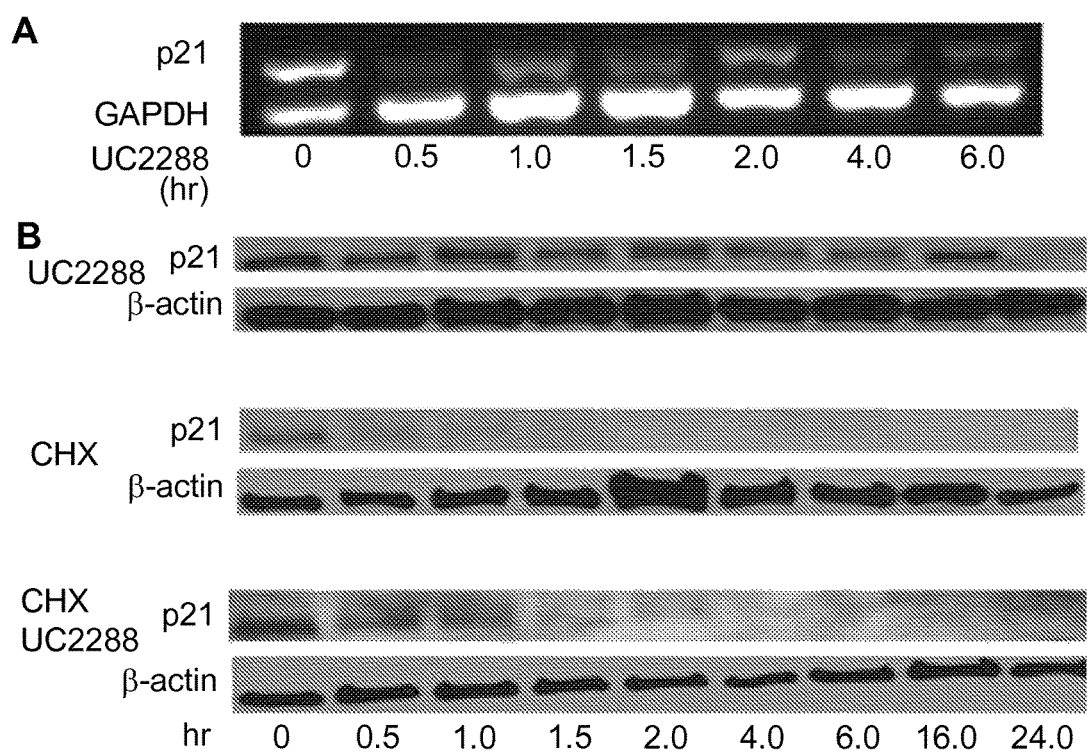
FIG. 3. Compound 2288 decreases p21 mRNA expression with no effect on p21 protein stability. 786-O cells were grown to confluence in 10% serum containing media and: (A) treated with Compound 2288 at 10 μM concentration or vehicle (DMSO) for the indicated time. mRNA was isolated and RT-PCR was performed as described in Materials and Methods. GAP DH is a loading control. (B) exposed to CHX (35 μM), Compound 2288 (10 μM). CHX (10 μg/ml) and Compound 2288 (10 μM), or vehicle (DMSO) for the indicated times and immunoblotting was performed with the antibodies indicated. β-actin is a loading control. The experiments shown are representative of at least 3 separate experiments.
Figure 4A:
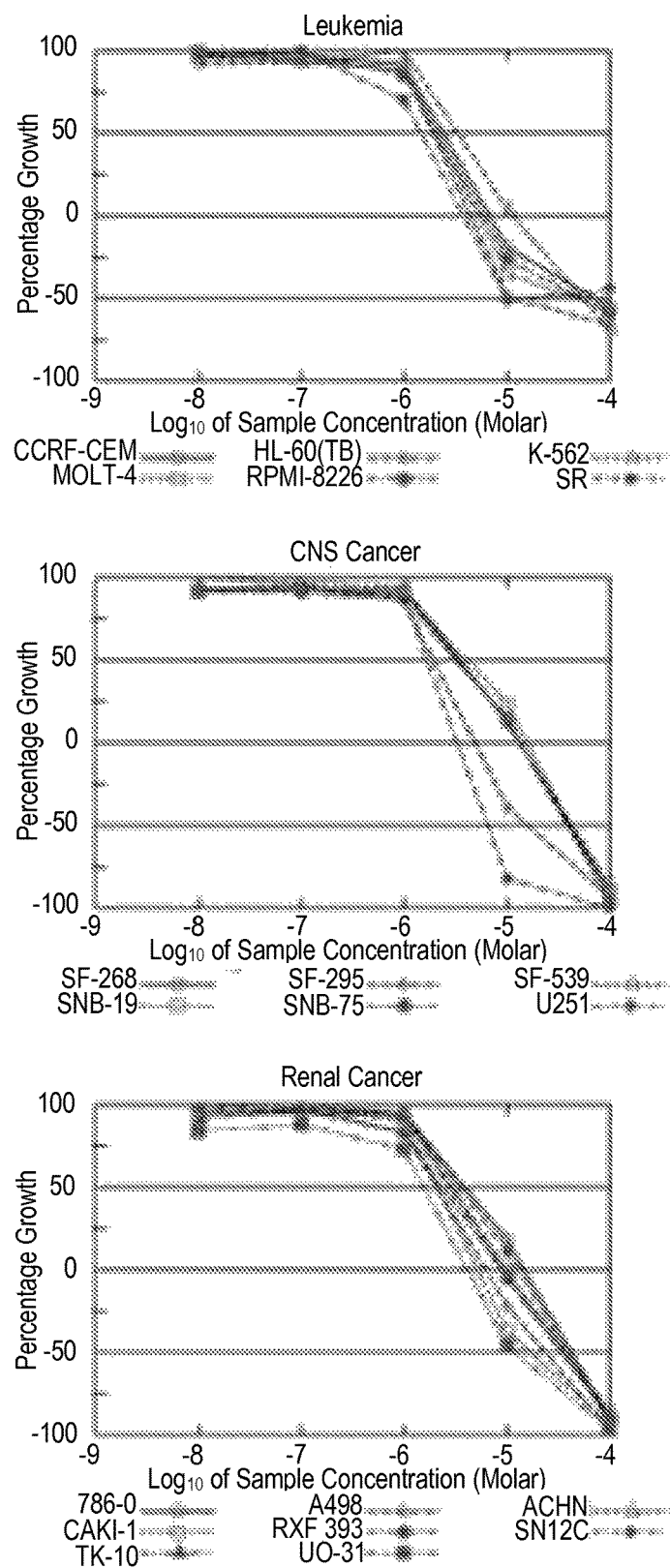
Figure 4B:
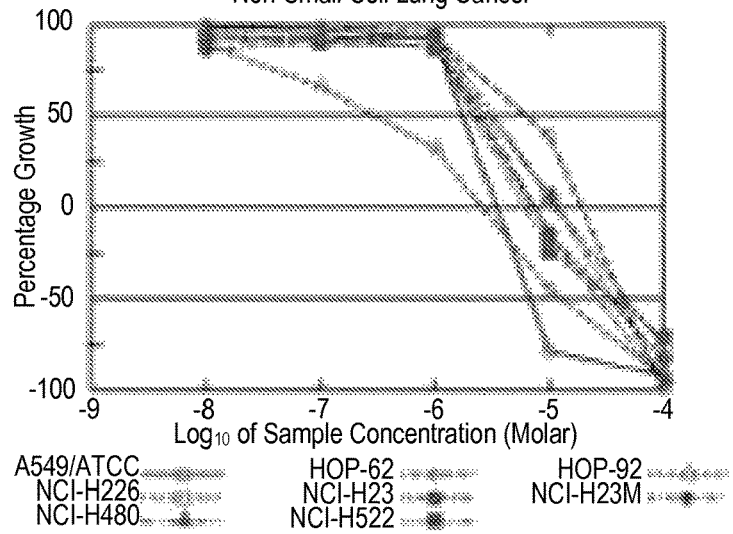
Figure 4B:
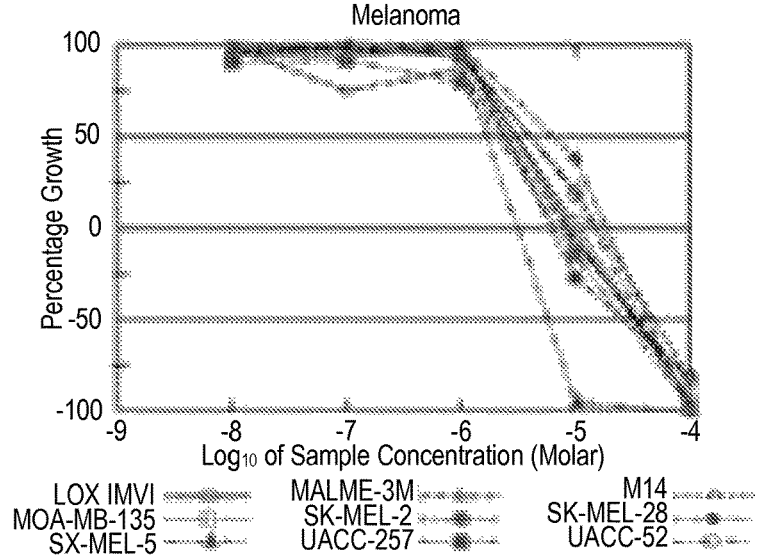
Figure 4B:
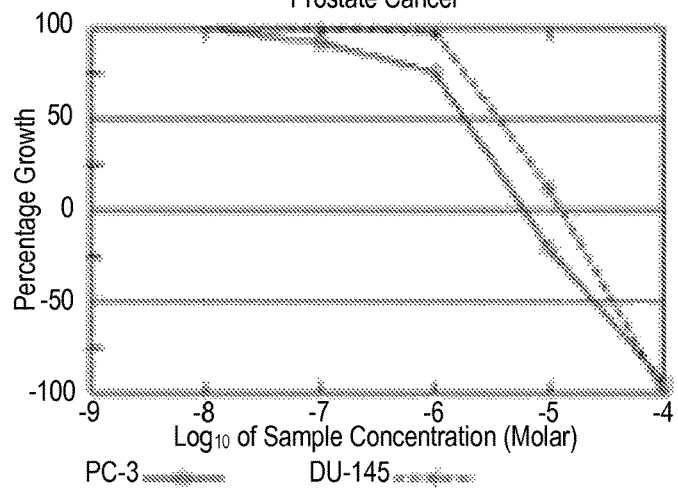
Figures 5, 6:
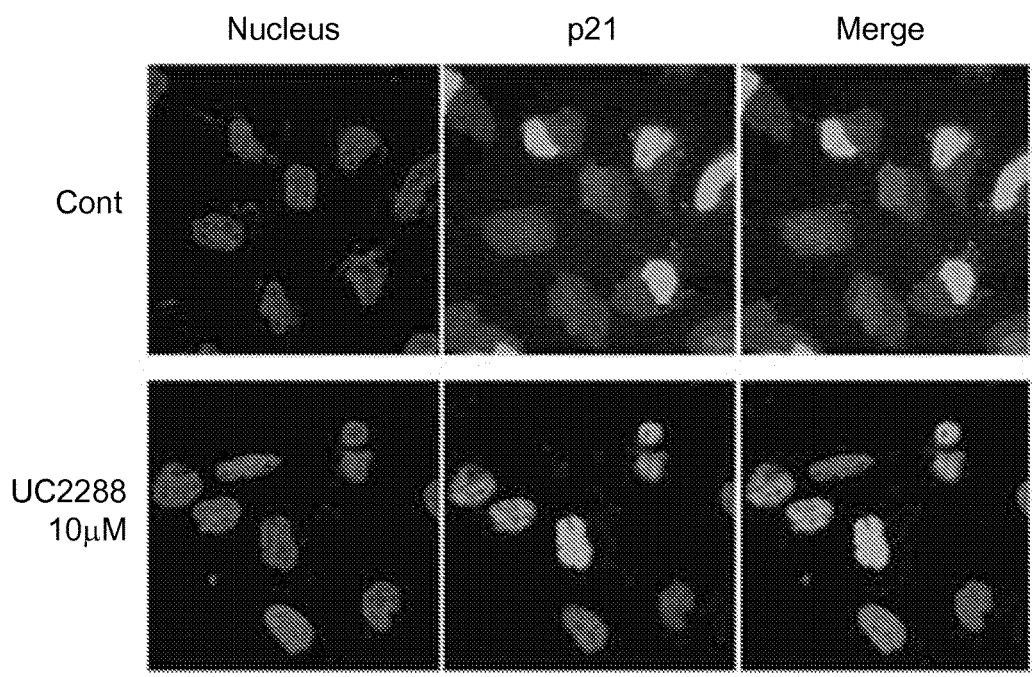
FIG. 5. Compound 2288 decreases cytosolic p21. 786-O cells were grown to confluence on 8-well chamber slides and treated with either Compound 2288 at 10 μM concentration or vehicle (DMSO) for 24 h. Immunofluorescence staining of p21 was visualized by confocal microscopy as described in Materials and Methods. p21 is green and the nuclear dye (DAPI) is blue. The experiment shown is representative of at least 3 separate experiments.
FIG. 6. Table of $IC_{50}$ values for C-Raf and B-Raf inhibition of sorafenib and Compound 2288, compared to VEGFR2 inhibition.

The present invention provides novel methods for the treatment of diseases mediated by the cyclin kinase inhibitor p21. The methods of the present invention are effective against such diseases through the inhibition of p21.

p21 is an intracellular protein which functions in the regulatory cascades responsible for cell cycle progression and apoptosis. Without being bound by any theory, cyclin kinase inhibitors, such as p21, are thought to regulate cell cycle progression by binding to cyclin/cdk pairs and inhibiting their downstream activity on retinoblastoma (Rb) protein. Consequently, the mitogenic transcription machinery is inhibited. Cyclin kinase inhibitors exert their anti-apoptotic effect by inhibiting the catalytic activities of kinases such as SAP and ASK1. Dysfunction of these regulatory cascades is a hallmark of cancer and other diseases.

Current chemotherapeutic agents for treating cancer can be divided into two classes: older generation agents which effect cell division or DNA synthesis; and newer generation agents which target specific molecular abnormalities in particular cancer types. Both classes have drawbacks. Older agents (e.g., cisplatin or nitrogen mustard) lack specificity in addition to being cytotoxic to both normal and malignant cells. Newer agents, such as Imatinib (Gleevec), are effective only against a narrow spectrum of cancers. Compounds which target p21 offer to fill this gap in the available chemotherapeutic arsenal by providing specificity and efficacy against a range of cancer types.

Cancer treatments (chemotherapy and radiation) are designed to terminally damage the DNA of cancer cells and thereby induce their apoptosis. p21 inhibits apoptosis thus reducing the effectiveness of these treatment modalities. p21 inhibitors offer to enhance the efficacy of these treatments by counteracting p21's anti-apoptotic function.

p21 can be targeted by any variety of mechanisms, such as by interfering with its catalytic or binding activities. Alternatively, p21 protein levels can be regulated by altering gene transcription using anti-sense or siRNA techniques. Anti-sense and siRNA techniques act by reducing messenger RNA (mRNA) levels which reduces protein (p21) levels since mRNA is translated to produce the target protein, so less mRNA results in production of less target protein (p21).

A compound of the present invention inhibits p21 activity, without limitation to any single theory or mode of action.

A link between cancer and p21 is observed. p21 overexpression is an early event in pancreatic neoplasms. High p21 levels are associated with poorer prognosis in breast cancer while p21 deficient cancers are more susceptible to chemotherapy. Several cancer types, such as oral, esophageal and breast have mutations in p21. Attenuating expression of p21 in colon cancer has salutary effects while modulating p21 sensitizes kidney cancer cells to chemotherapy.

Accordingly, without being bound by any theory, the compounds and compositions of the present invention cause dose-dependent cytotoxicity as well as apoptosis when exposed to cancer cells. In addition, under some conditions, the compounds and compositions work synergistically with other cancer treatment agents, such as doxorubicin, such that lower doses of the other cancer treatment agents may be necessary.

II. Definitions

As used herein, the terms "treat", "treating" and "treatment" refer to any indicia of success in the treatment or amelioration of an injury, pathology, condition, or symptom (e.g., pain), including any objective or subjective parameter such as abatement: remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter: including, e.g., the result of a physical examination.

As used herein, the term "disease mediated by p21" and the like refers to a disease or condition characterized by less than or greater than normal p21 activity. A disease or condition mediated by p21 is one in which modulation of p21 results in some effect on the underlying condition or disease (e.g., a p21 inhibitor or antagonist results in some improvement in patient well-being in at least some patients). Exemplary p21-mediated diseases include, but are not limited to, cancer and atherosclerosis.

The term "modulate" refers to the ability of a compound to increase or decrease the function, or activity, of the associated activity (e.g., p21). "Modulation", as used herein in its various forms, is meant to include antagonism and partial antagonism of the activity associated with p21.

"Inhibition", "inhibits" and the like refer to a method of binding to and/or partially or totally blocking or prohibiting a specific activity or function, e.g. the activity associated with p21. Inhibitors of p21 are compounds that, e.g., bind to p21 and/or partially or totally block p21 activity.

As used herein, "administering" refers to oral administration, administration as a suppository, topical contact, parenteral, intravenous, intraperitoneal, intramuscular, intralesional, intranasal or subcutaneous administration, intrathecal administration, or administration using a medical device, such as a catheter, a balloon, an implantable device (e.g., a mini-osmotic pump), a prosthesis, a graft, or a stent, to the subject.

As used herein, the term "cancer" refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells can exist alone within an animal, or can circulate in the blood stream as independent cells, such as leukemic cells. "Cancer" includes, but is not limited to the following cancers: breast, ovarian, cervical, prostate, testical, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver and biliary passages (e.g., liver hepatocellular carcinoma (HCC)), kidney (e.g., renal cell carcinoma (RCC)), myeloid disorders, lymphoid disorders, Hodgkin's, hairy cells, buccal cavity and pharynx (oral). lip, tongue, mouth, pharynx, small intestine, colorectal, large intestine, rectum, brain and central nervous system, and leukemia.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "therapeutically effective amount" refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "alkyl" refers to a saturated hydrocarbon which may be straight-chain such as ethyl, or branched-chain such as isopropyl, t-amyl, or 2,5-dimethylhexyl. This definition applies both when the term is used alone and when it is used as part of a compound term, such as "arylalkyl," "alkylamino" and similar terms. In some embodiments, alkyl groups are those containing 1 to 24 carbon atoms. All numerical ranges in this specification and claims are intended to be inclusive of their upper and lower limits. Additionally, the alkyl and heteroalkyl groups may be attached to other moieties at any position on the alkyl or heteroalkyl group which would otherwise be occupied by a hydrogen atom, for example, 2-pentyl, 2-methylpent-1-yl or 2-propyloxy group. Divalent alkyl groups may be referred to as "alkylene," and divalent heteroalkyl groups may be referred to as "heteroalkylene," such as those groups used as linkers in the present invention. The alkyl, alkylene, and heteroalkylene moieties may also be optionally substituted with halogen atoms, or other groups such as oxo, cyano, nitro. alkyl, alkylamino, carboxyl, hydroxyl, alkoxy, aryloxy, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_3$-$C_8$ cycloalkyl includes cyclopropyl, cyclobutyl, cyclopentyl, cyclohexyl, cycloheptyl, and cyclooctyl, Cycloalkyl also includes norbornyl and adamantyl.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. Some heterocycloalkyl groups have from 3 to 8 ring members and from 1 to 3 heteroatoms such as N, O and S. For example, heterocycloalkyl includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl. Exemplary 5- to 6-membered heterocycloalkyl rings containing nitrogen include, but are not limited to, pyrrolidine, piperidine, morpholine and piperazine.

As used herein, the term "halogen" refers to fluorine, chlorine, bromine and iodine.

As used herein, the term "haloalkyl" refers to alkyl as defined above where some or all of the hydrogen atoms are substituted with halogen atoms. For example, haloalkyl includes trifluoromethyl, fluoromethyl, etc. The term "perfluoro" defines a compound or radical which has at least two available hydrogens substituted with fluorine. For example, perfluoromethane refers to 1,1,1-trifluoromethyl. and perfluoromethoxy refers to 1,1,1-trifluoromethoxy.

As used herein, the term "alkoxy" refers to alkyl with the inclusion of an oxygen atom, for example, methoxy, ethoxy. etc. "Haloalkoxy" is as defined for alkoxy where some or all of the hydrogen atoms are substituted with halogen atoms. For example, haloalkoxy includes trifluoromethoxy, etc. Additionally, terms such as "haloalkyl," and "haloalkoxy" are meant to include monohaloalkyl(oxy) and polyhaloalkyl(oxy). For example, the term "$C_1$-$C_6$ haloalkyl" is mean to include trifluoromethyl, 2,2,2-trifluoroethyl, 4-chlorobutyl, 3-bromopropyl, and the like.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid. propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

III. Compounds

The compounds of the present invention are sorafenib derivatives having the formula:

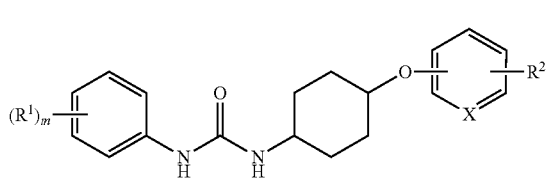

(I)

wherein $R^1$ is halogen, $C_{1-6}$ haloalkyl or $C_{1-6}$ haloalkoxy; $R^2$ is —CN, $C_{1-6}$ haloalkyl, $C_{1-6}$ haloalkoxy, —C(O)OR$^{2a}$ or —C(O)NR$^{2a}$R$^{2b}$; $R^{2a}$ and $R^{2b}$ are each independently H, $C_{1-6}$ alkyl or $C_{3-8}$ cycloalkyl, or are taken together to form a 5- or 6-membered heterocycloalkyl ring; X is —CH— or —N—; and the subscript m is an integer from 1 to 3; such that when X is —CH—, $R^2$ is —C(O)OH, and subscript m is 1, then $R^1$ is halogen or $C_{1-6}$ haloalkyl. The present invention also includes salts and isomers of the compounds of Formula I.

In some embodiments, the compound has the formula:

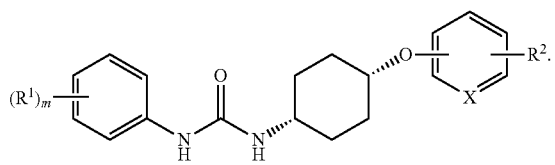

In other embodiments, the compound has the formula:

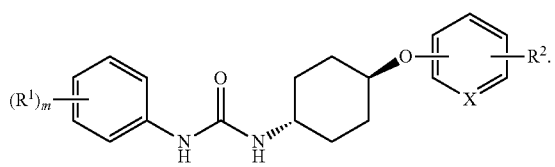

In some embodiments, $R^1$ is Cl, F, Br, I, $CF_3$ or $CF_3O$. In other embodiments, $R^2$ is —CN or —C(O)NR$^{2a}$R$^{2b}$.

In other embodiments, X is —CH—. In some other embodiments, X is —N—. In still other embodiments, the subscript m is 1 or 2.

In another embodiment, the compound has the formula:

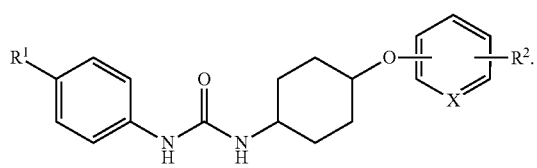

In some embodiments, the compound has the formula:

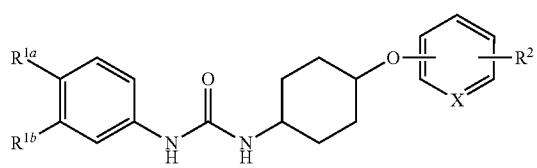

wherein $R^{1a}$ and $R^{1b}$ are each independently halogen, $C_{1-6}$ haloalkyl or $C_{1-6}$ haloalkoxy. In other embodiments, the compound has the formula:

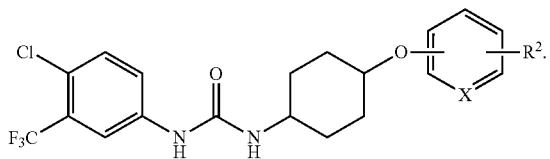

In still other embodiments, the compound has the formula:

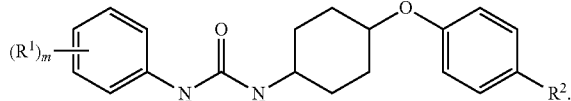

In other embodiments, the compound has the formula:

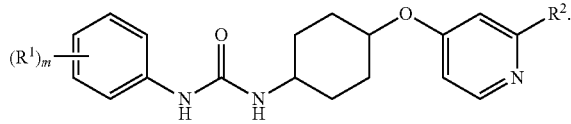

In other embodiments, the compound has the formula:

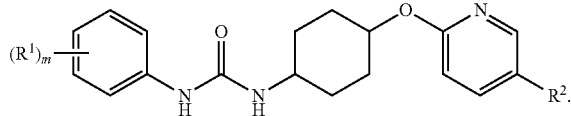

In other embodiments, the compound has the formula:

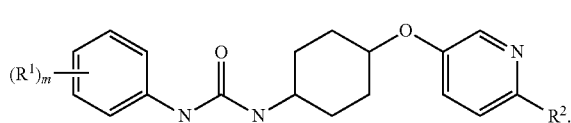

In other embodiments, the compound has the formula:

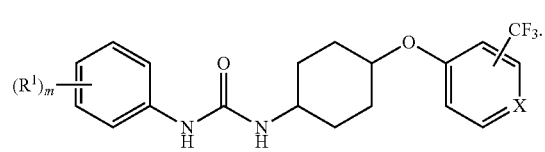

In other embodiments, the compound has the formula:
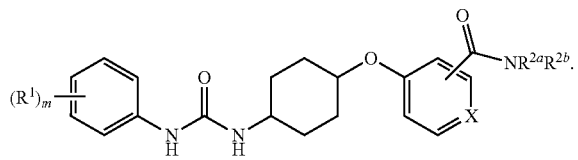
In other embodiments, the compound has the formula:
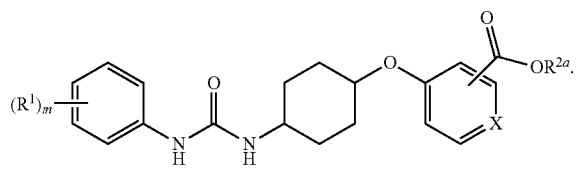
In other embodiments, the compound has the formula:
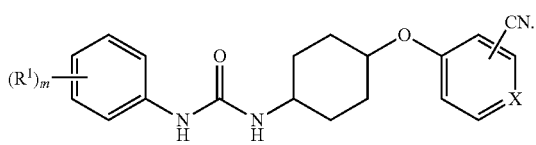
In other embodiments, the compound is:
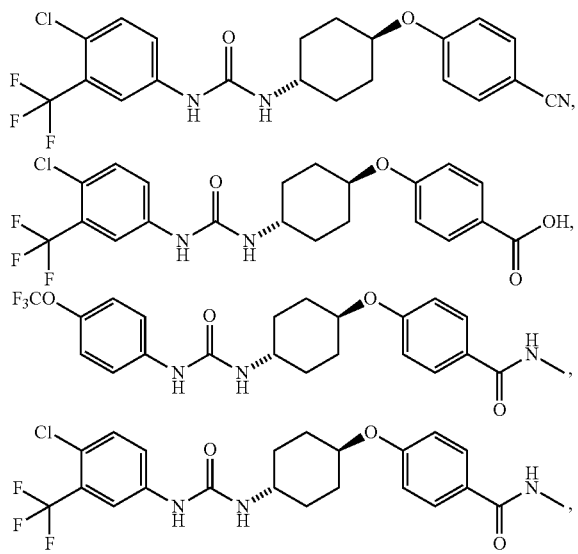
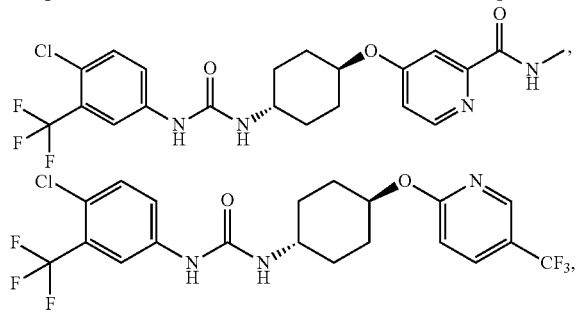
-continued
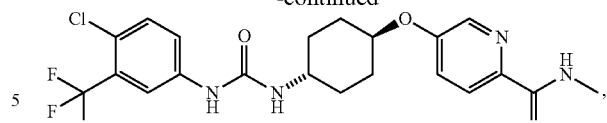
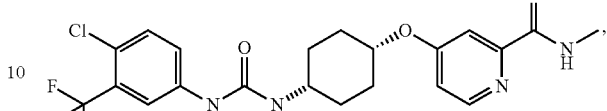
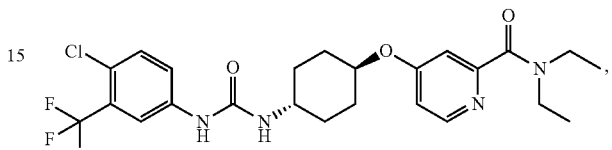
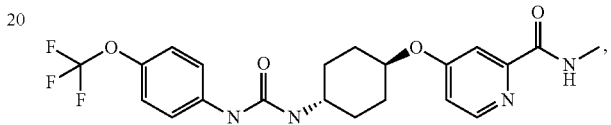
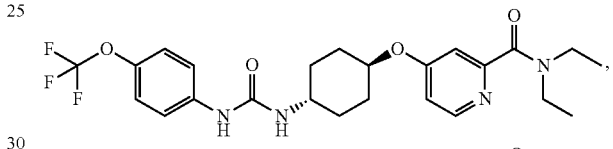
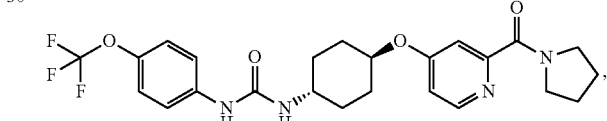
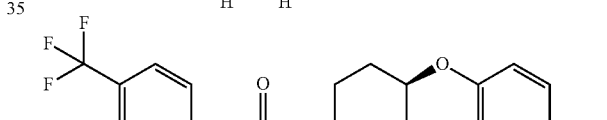
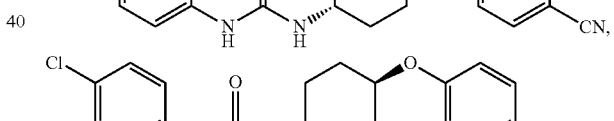
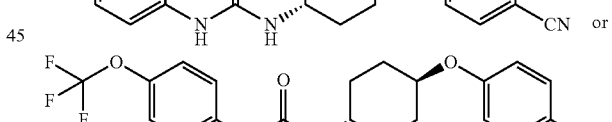
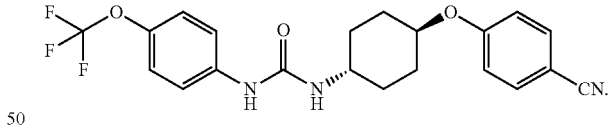
In other embodiments, the compound is:
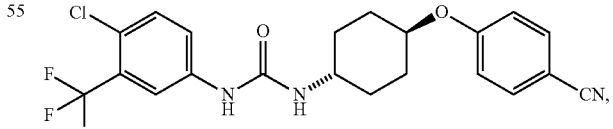
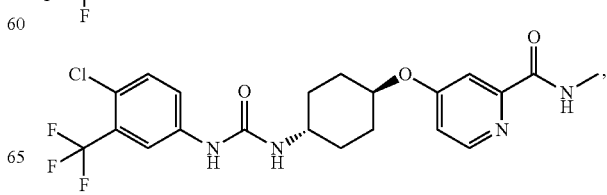

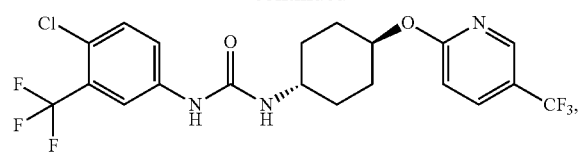
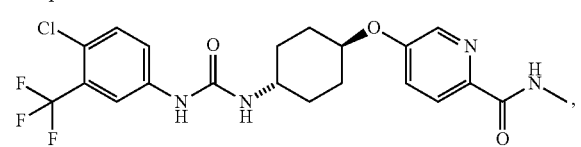
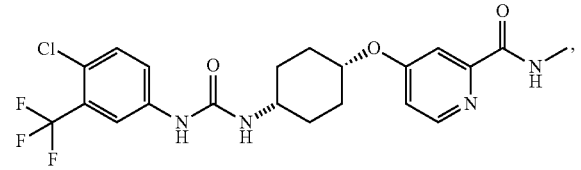
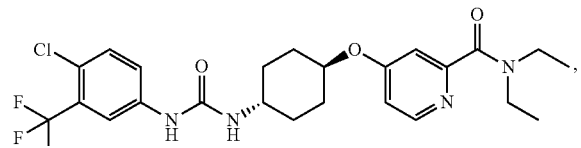
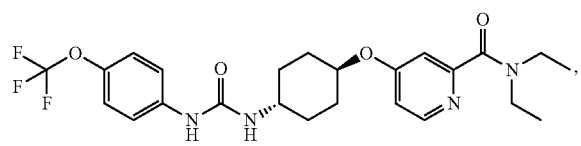
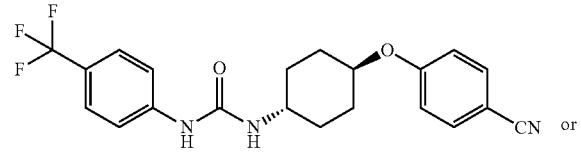
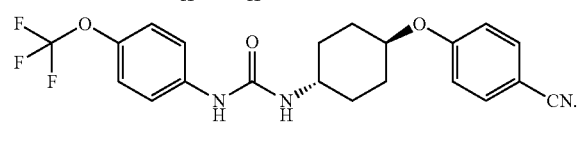
In other embodiments, the compound is:
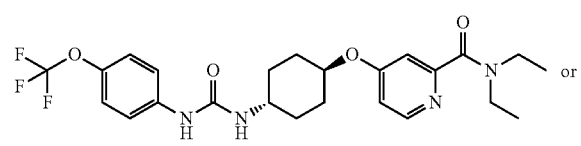
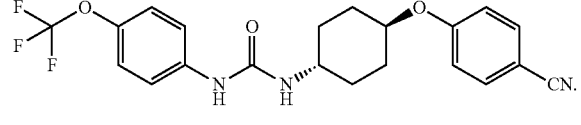
In other embodiments, the compound can be:
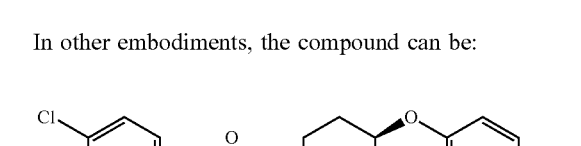
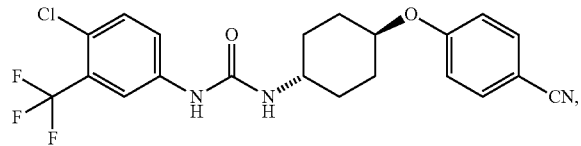 [SMILES: O=C(Nc1ccc(Cl)c(C(F)(F)F)c1)N[C@H]1CC[C@H](Oc2ccc(C(F)(F)F)cn2)CC1]
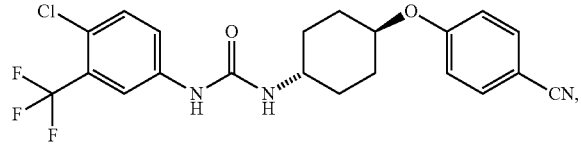
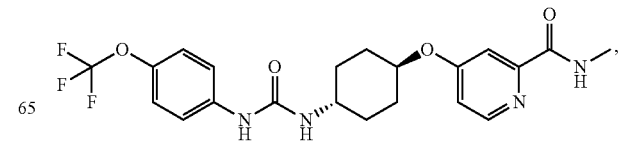

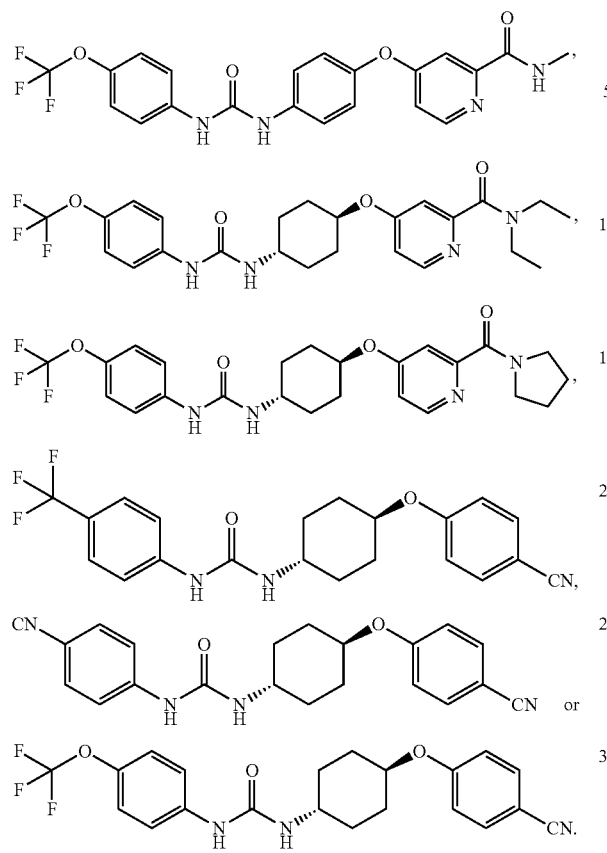

In other embodiments, the compound can be:

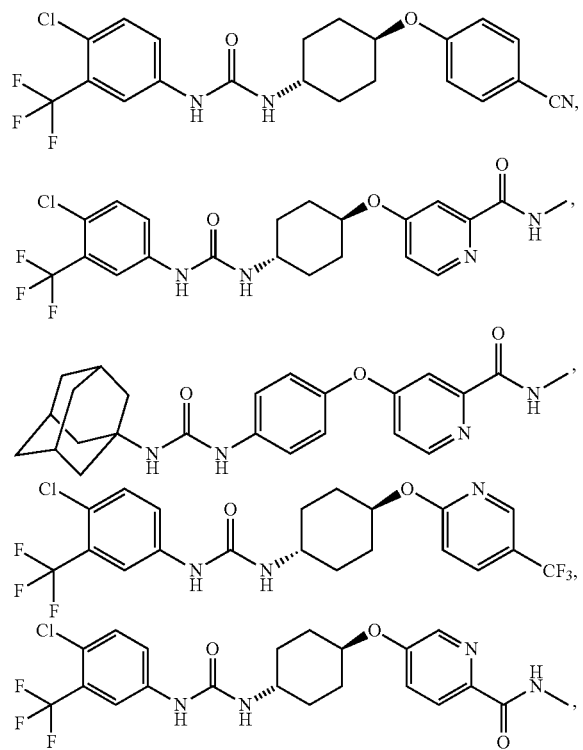

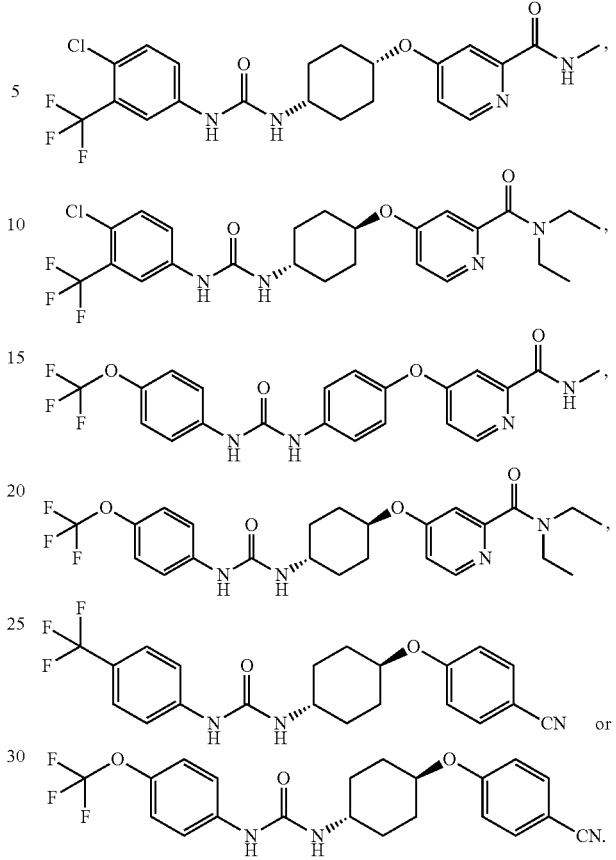

In some embodiments, the compound has the structure:

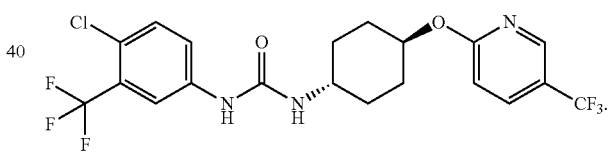

Certain compounds of the present invention possess asymmetric carbon atoms (optical centers) or double bonds; the racemates, diastereomers. geometric isomers and individual isomers are all intended to be encompassed within the scope of the present invention.

The compounds of the present invention can be prepared by a variety of methods known to one of skill in the art, such as described in International Patent Application No. PCT/US2012/025074, or in Richard C. Larock, *Comprehensive Organic Transformations* 1989, VCH Publishers, Inc.

IV. Pharmaceutical Compositions

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets. gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular. intravaginal, and intrarectal routes including suppositories, insufflation, powders and aerosol formulations (for examples of steroid inhalants, see Rohatagi, *J. Clin. Pharmacol.* 35:1187-1193. 1995; Tjwa. Ann. Allergy Asthma Immunol. 75:107-111. 1995). Accordingly. the present invention also provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers. adjuvants, diluents, tissue permeation enhancers, solubilizers, and the like. Preferably, the composition will contain about 0.01% to about 90%, preferably about 0.1% to about 75%, more preferably about 0.1% to 50%. still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES supra.

Suitable solid excipients include, but are not limited to, magnesium carbonate; magnesium stearate; calcium phosphate; calcium silicate; talc; pectin; dextran, dextrin. and cyclodextrin inclusion complexes; a low melting wax; cocoa butter; carbohydrates; sugars including, but not limited to, lactose, dextrose, sucrose, mannitol, or sorbitol; starches including, but not limited to, starch from corn. wheat, rice, potato, or other plants; cellulose such as methyl cellulose, hydroxypropylmethyl-cellulose. or sodium carboxymethylcellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981. etc.; lubricating agents; mineral oil; wetting agents; emulsifying agents; suspending agents; preserving agents such as methyl-, ethyl-, and propyl-hydroxy-benzoates (i.e., the parabens);

pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption. or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin. as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners. solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

V. Administration

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone.

The compositions containing a compound or a combination of compounds of the present invention may be administered repeatedly, e.g., at least 2, 3, 4, 5, 6, 7, 8, or more times, or the composition may be administered by continuous infusion. Suitable sites of administration include, but are not limited to. skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a compound or a combination of compounds. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see. for example, REMINGTON'S PHARMACEUTICAL SCIENCES, 18TH ED., Mack Publishing Co., Easton, Pa. (1990)). The composition to be administered contains a quantity of the compound or combination of compounds in a pharmaceutically effective amount for relief of a condition being treated (e.g. osteoporosis) when administered in accordance with the teachings of this invention. In addition, pharmaceutically acceptable salts of the compounds of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4$^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the compounds or combination of compounds, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The compounds can also be formulated into a suppository disposed, for example, in a polyethylene glycol (PEG) carrier.

Liquid compositions can be prepared by dissolving or dispersing a compound or a combination of compounds and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compounds of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer. e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the compound to the appropriate site or sites. However, one of ordinary skill in the art understands that the dose administered will vary depending on a number of factors, including, but not limited to, the particular compound or set of compounds to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the compounds of the present invention permits a wider margin of safety for dosage concentrations and for repeated dosing.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intraarterial, intraventricular, intraatrial, intraaortal, intramuscular, intrasternal, intracavernous. intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium. mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate. polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Methods

The compounds of the present invention are useful for the treatment of cancer and other diseases, as well as the inhibition of p21. Over-expression or increased cytoplasmic p21 is associated with a variety of disease conditions, such as cancer. Accordingly, inhibitors of p21, such as the compounds of the present invention, are useful for the treatment of a variety of disease states, such as cancer.

A. Methods of Treating Diseases Mediated by p21

In some embodiments, the present invention provides a method of treating a disease mediated by p21, the method including administering to a subject in need thereof a therapeutically effective amount of a compound of the present invention, thereby treating the disease. Diseases mediated by p21 that can be treated using the present invention include, but are not limited to, cancer and atherosclerosis.

In some embodiments, the present invention provides a method of treating cancer, the method including administering to a subject in need thereof, a therapeutically effective amount of a compound of the present invention, thereby treating cancer. The cancer can be any cancer known to one of skill in the art, such as, leukemia, CNS, renal, non-small cell lung cancer, melanoma, prostate, kidney, liver, breast, ovarian, pancreatic or colorectal cancer. In some other embodiments, the cancer is kidney cancer. In other embodiments, the cancer is liver cancer. In still other embodiments, the cancer is breast cancer. In still other embodiments, the cancer is colorectal cancer. In some embodiments, the cancer is renal cell carcinoma (RCC), hepatocellular carcinoma (HCC), breast cancer or colorectal cancer.

The compounds and compositions of the present invention can be combined with any other suitable agent. In some embodiments, the method further includes administering to the subject a therapeutically effective amount of a chemotherapeutic agent. Suitable chemotherapeutic agents include, but are not limited to, doxorubicin, cisplatinum, cyclophosphamide, chlorambucil and nitrogen mustard, and combinations thereof. In some embodiments, the chemotherapeutic agent is doxorubicin.

The components of the combination can be administered together or separately. The components of the combination can be administered simultaneously, during the same hour, day, week or month, or during the same therapy. The components of the combination or the combination thereof can be administered periodically, e.g. hourly, daily, weekly or biweekly, or monthly, depending on the patient's needs. Alternatively, the components of the combination or the combination can be administered several times a day, several times a week, several times a month or several times a year.

In some embodiments, the present invention provides a method of treating cancer, the method including contacting cancer cells with a therapeutically effective amount of a compound of the present invention, thereby treating cancer. The contacting can be in vivo or in vitro. In some embodiments, the contacting is performed in vitro.

The methods generally involve administering to a subject in need of such treatment an effective amount of a compound of the present invention. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

B. Methods of Inhibiting p21

In other embodiments, the present invention provides a method of inhibiting p21, the method including contacting p21 with a compound of the present invention in an amount sufficient to inhibit p21, thereby inhibiting p21. The contacting can be in vivo or in vitro. In some embodiments, the contacting is performed in vitro.

VII. Assays to Identify Compounds that Inhibit p21

The compounds of the present invention can be identified as inhibitors of p21 by a variety of assays and methods known to one of skill in the art. In one embodiment, the compounds of the present invention can be screened using a cell-based assay.

The cell-based assay can be performed using any suitable cell line, such as renal cell carcinoma (RCC) and HepG2 hepatoma cell line. The cells are placed in suitable a medium, such as fetal bovine serum, with an optional antibiotic such as penicillin-streptomycin. The cells are plated, and the inhibitors added at specific concentrations. Cell viability can be determined at any time after contact with the inhibitors, such as 72 hours. Cellular proliferation can be determined using any method known in the art, including colorimetric methods.

Further analysis of p21 inhibition can be performed by immunoblotting using an appropriate p21 antibody.

Kinase-based assays, for example, to identify compounds that selectively inhibit p21 without inhibiting other kinases, can be performed using any kinase known, such as Raf-1 or b-Raf, among others. Any suitable substrate can also be used, such as MEK1. The assay can be performed using luminescence as the detection method.

In some embodiments, p21 inhibitors are identified using the assay described in Example 1.

The following examples are provided to illustrate the invention and are not intended to limit any aspect of the invention as set forth above or in the claims below.

VIII. Examples

Example 1

Identification of Compounds that Inhibit p21 by Immunoblotting

Cells harvested after growth to confluence in 10% serum-containing media and treatment with compounds of the invention were washed with phosphate buffered saline (PBS) and lysed in lysis buffer composed of 50 mM HEPES, 1% Triton X-100, 10 mM sodium pyrophosphate, 100 mM sodium fluoride and 4 mM EDTA at 4° C. Cell lysates were pelleted. Supernatants were electrophoresed and immunoblotted. Membranes were blocked in 5% nonfat dry milk for 30 min at room temperature and probed with p21 antibody. Membranes were then probed with horseradish peroxidase tagged anti-mouse or anti-rabbit IgG antibodies (diluted 3:20,000 and 3:10,000 in 5% nonfat dry milk, respectively) for 2 h at room temperature. Signal was detected using enhanced chemiluminescence (ECL) solutions. Table 1 shows the p21 levels determined in ACHN and/or 786-O cells at 24 h of culture with compounds of the invention.

TABLE 1

Inhibitory activities against human sEH and Raf kinases (% inhibition at 10 μM concentration) and the effects of sorafenib derivatives on p21 expression.

| Compound | Structure | % Inhibition (IC$_{50}$) Human sEH (nM) | Raf-1 (nM) | b-Raf (V600E) (nM) | p21 inhibition |
|---|---|---|---|---|---|
| Sorafenib | 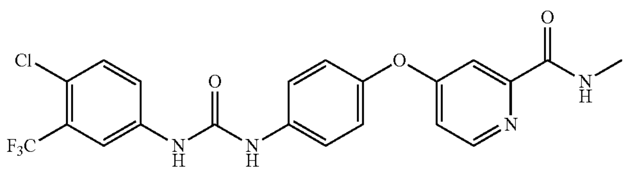 [SMILES: CNC(=O)c1cc(Oc2ccc(NC(=O)Nc3ccc(Cl)c(C(F)(F)F)c3)cc2)ccn1] | 12 ± 2 | 45 ± 5 | 12.7 ± 1.5 | + |
| 1163 | 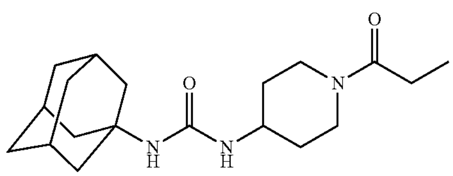 [SMILES: CCC(=O)N1CCC(NC(=O)NC23CC4CC(CC(C4)C2)C3)CC1] | 3.2 | ND | ND | − |
| 1471 (t-AUCB) | 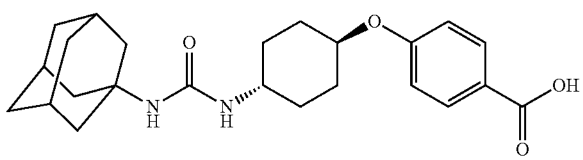 [SMILES: O=C(NC12CC3CC(CC(C3)C1)C2)N[C@H]1CC[C@H](Oc2ccc(C(=O)O)cc2)CC1] | 1.5 | ND | ND | − |
| 1709 | 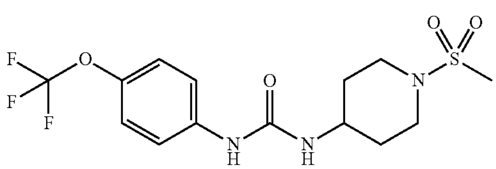 [SMILES: CS(=O)(=O)N1CCC(NC(=O)Nc2ccc(OC(F)(F)F)cc2)CC1] | 2.9 | ND | ND | − |
| 1728 (t-TUCB) | 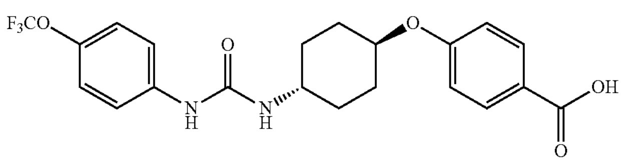 [SMILES: O=C(Nc1ccc(OC(F)(F)F)cc1)N[C@H]1CC[C@H](Oc2ccc(C(=O)O)cc2)CC1] | 0.9 ± 0.1 | >10000 | ND | − |
| 1770 TPPU | 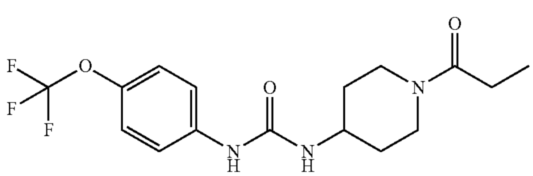 [SMILES: CCC(=O)N1CCC(NC(=O)Nc2ccc(OC(F)(F)F)cc2)CC1] | 3.7 | ND | ND | − |
| 2182 SHH06057 | 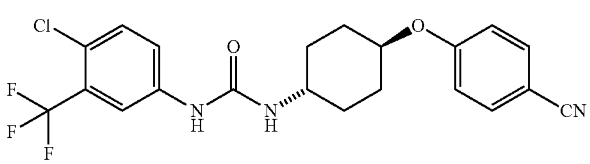 | 14.6 | ND | ND | + |
| 2221 SHH06071 | 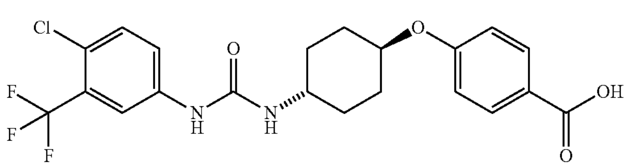 | 0.5 | 4300 ± 400 | >10000 | − |

TABLE 1-continued

Inhibitory activities against human sEH and Raf kinases (% inhibition at 10 μM concentration) and the effects of sorafenib derivatives on p21 expression.

| Compound | Structure | % Inhibition (IC$_{50}$) | | | p21 inhibition |
| --- | --- | --- | --- | --- | --- |
| | | Human sEH (nM) | Raf-1 (nM) | b-Raf (V600E) (nM) | |
| 2225 SHH06094 | 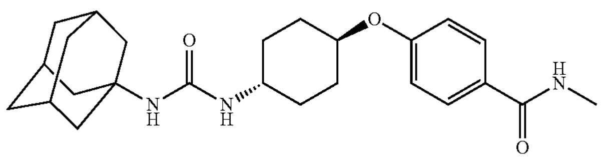 [SMILES: CNC(=O)c1ccc(O[C@H]2CC[C@H](NC(=O)NC34CC5CC(CC(C5)C3)C4)CC2)cc1] | 0.5 | >10000 | ND | – |
| 2227 SHH06097 | 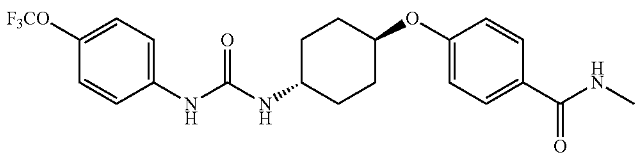 [SMILES: CNC(=O)c1ccc(O[C@H]2CC[C@H](NC(=O)Nc3ccc(OC(F)(F)F)cc3)CC2)cc1] | 0.5 | 340 ± 40 | >10000 | – |
| 2253 SHH06096 | 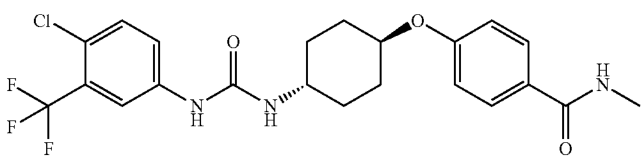 [SMILES: CNC(=O)c1ccc(O[C@H]2CC[C@H](NC(=O)Nc3ccc(Cl)c(C(F)(F)F)c3)CC2)cc1] | 0.5 | 340 ± 40 | >10000 | – |
| 2278 t-CUPM SHH07095 | 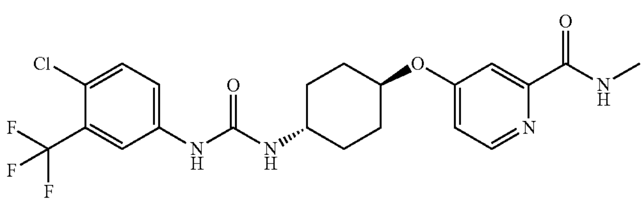 [SMILES: CNC(=O)c1cc(O[C@H]2CC[C@H](NC(=O)Nc3ccc(Cl)c(C(F)(F)F)c3)CC2)ccn1] | 0.5 | 75 ± 5 | 1,500 ± 100 | + |
| 2287 SHH08002 | 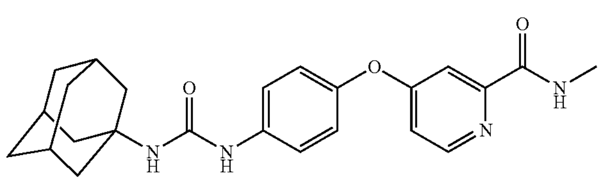 [SMILES: CNC(=O)c1cc(Oc2ccc(NC(=O)NC34CC5CC(CC(C5)C3)C4)cc2)ccn1] | 0.5 | >10000 | >10000 | ND |
| 2288 SHH08006 | 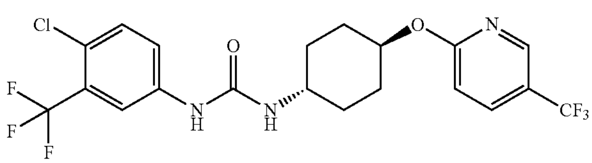 [SMILES: O=C(Nc1ccc(Cl)c(C(F)(F)F)c1)N[C@H]1CC[C@H](Oc2ccc(C(F)(F)F)cn2)CC1] | 0.5 | >10000 | >10000 | + |
| 2316 SHH08050 | 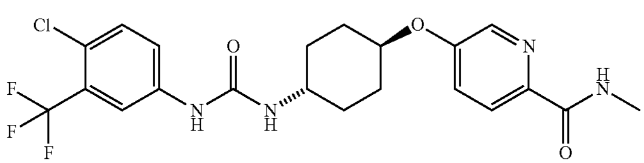 | 0.5 | 175 ± 20 | 200 ± 150 | + |
| 2319 SHH08049 | 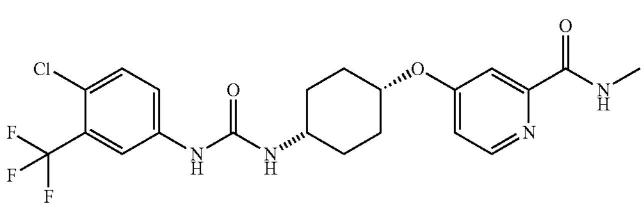 | 0.5 | 535 ± 100 | 5000 ± 500 | + |

TABLE 1-continued

Inhibitory activities against human sEH and Raf kinases (% inhibition at 10 μM concentration) and the effects of sorafenib derivatives on p21 expression.

| Compound | Structure | % Inhibition (IC$_{50}$) | | | p21 inhibition |
|---|---|---|---|---|---|
| | | Human sEH (nM) | Raf-1 (nM) | b-Raf (V600E) (nM) | |
| 2574 SHH09039 | 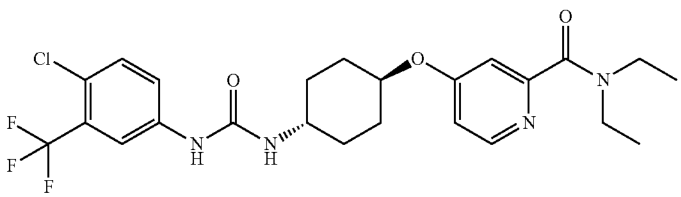 [SMILES: CCN(CC)C(=O)c1cc(O[C@H]2CC[C@H](NC(=O)Nc3ccc(Cl)c(C(F)(F)F)c3)CC2)ccn1] | 0.5 | >10000 | ND | + |
| 2575 SHH09040 | 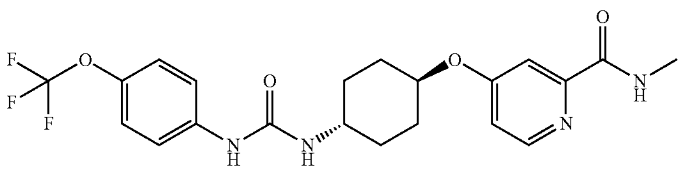 [SMILES: CNC(=O)c1cc(O[C@H]2CC[C@H](NC(=O)Nc3ccc(OC(F)(F)F)cc3)CC2)ccn1] | 0.5 | >10000 | ND | − |
| 2576 SHH09038 | 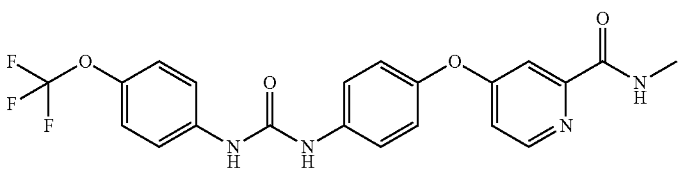 [SMILES: CNC(=O)c1cc(Oc2ccc(NC(=O)Nc3ccc(OC(F)(F)F)cc3)cc2)ccn1] | 0.5 | 30 | ND | + |
| 2577 SHH09041 | 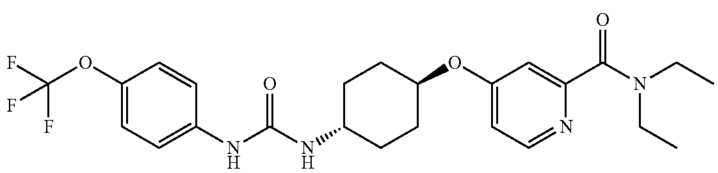 [SMILES: CCN(CC)C(=O)c1cc(O[C@H]2CC[C@H](NC(=O)Nc3ccc(OC(F)(F)F)cc3)CC2)ccn1] | 0.5 | ND | ND | + |
| 2578 SHH09042 | 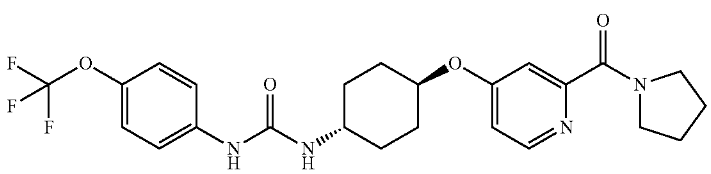 [SMILES: O=C(Nc1ccc(OC(F)(F)F)cc1)N[C@H]1CC[C@H](Oc2ccnc(C(=O)N3CCCC3)c2)CC1] | 0.5 | ND | ND | − |
| 2579 Syn034 | 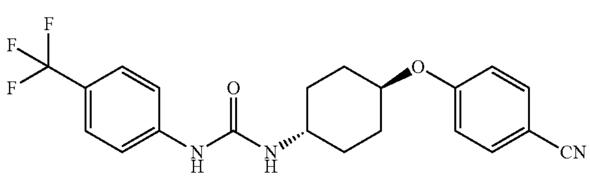 [SMILES: N#Cc1ccc(O[C@H]2CC[C@H](NC(=O)Nc3ccc(C(F)(F)F)cc3)CC2)cc1] | 0.5 | ND | ND | + |
| 2580 SHH05013 | 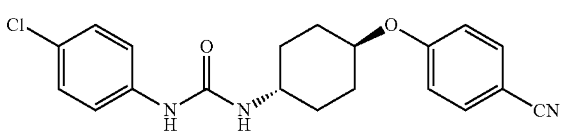 [SMILES: N#Cc1ccc(O[C@H]2CC[C@H](NC(=O)Nc3ccc(Cl)cc3)CC2)cc1] | 0.5 | ND | ND | ND |
| 2581 SHH08010 | 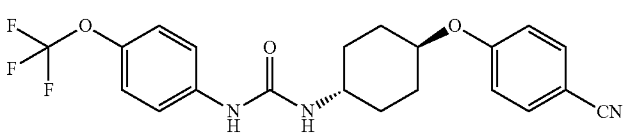 [SMILES: N#Cc1ccc(O[C@H]2CC[C@H](NC(=O)Nc3ccc(OC(F)(F)F)cc3)CC2)cc1] | 0.5 | ND | ND | + |

+ denotes inhibition of p21 secretion or the absence of p21
− denotes the presence of p21
ND: not determined

Example 2

Inhibition and Cell Viability Activity

Cell Lines.

A normal human kidney primary proximal tubule epithelial cell line (HK2) and three human proximal tubule epithelial cancer cell lines (786-0, Caki-1, and ACHN) were obtained from the American Type Culture Collection (Rockville, Md.), and the human ovarian carcinoma cell line (Hey) was generously provided by Dr. Erin Dickerson, University of Minnesota. HK2 and ACHN cells were maintained in Dulbecco's modified Eagle's medium supplemented with 10% fetal bovine serum (FBS), 100 units/mL streptomycin, and 100 mg/mL penicillin. 786-0. Caki-1, and Hey cells were maintained in RPMI supplemented with 10% FBS, 100 units/mL streptomycin, and 100 mg/mL penicillin. Cells were maintained at 5% $CO_2$ at 37° C.

Materials.

CHX and dimethyl sulfoxide (DMSO) was obtained from Sigma (St. Louis, Mo., USA). Compound 2288 and CHX were dissolved in DMSO. Mouse monoclonal anti-p21WAF1/Cip antibody was obtained from Millipore (Billerica, Mass., USA). Mouse monoclonal anti-phosphor Akt antibody, mouse monoclonal anti-p53 antibody, rabbit monoclonal anti-phospho ERK, rabbit monoclonal anti-p21WAF1/Cip antibody, and anti-rabbit IgG (H+L), F(ab')2 Fragment (Alexa Fluork 488 Conjugate) antibody were obtained from Cell Signaling Technology, Inc. (Beverly, Mass. USA). Goat anti-mouse and goat anti-rabbit HRP conjugated IgG were obtained from Bio-Rad (Hercules, Calif., USA). ECL Plus Western Blotting Detection Reagents was obtained from GE Healthcare (Piscataway, N.J., USA). VECTASHIELD HardSet Mounting Medium with DAPI was obtained from Vector Laboratories (Burlingame, Calif., USA).

Assay for Recombinant Raf Kinase Inhibition.

$IC_{50}$ values were calculated by quantifying the end-point ADP production from each kinase reaction using the ADP-Glo™ Kinase Assay kit (Promega, Madison, Wis.) according to the manufacturer's instructions. Reactions were performed in Tris buffer (50 mM pH 7.5, rt) containing 20 mM $MgCl_2$ and 0.1% bovine serum albumin. Full length recombinant Raf-I and b-Raf (V600E) kinases, and their respective substrate, recombinant MEK-1, were purchased from US Biological (Swampscott, Mass.). All assays were performed using 10 nM Raf kinase, 1 μM MEK-1, 10 μM ATP, at 22° C. for 1 hour. Inhibitors were dissolved in DMSO and $IC_{50}$ values were obtained by measuring the change in the ADP production (luminescent signal intensity) at various inhibitor concentrations as compared to the control. Individual data sets were performed in duplicate and each $IC_{50}$ value was determined from three separate experiments. The data were fit to a saturation curve using KaleidaGraph graphing program (Synergy Software) to determine the $IC_{50}$ values.

Inhibitory Assay of Recombinant VEGFR-2 Activity.

Inhibition of kinases was screened by the KinaseSeeker™ assay with Luceome Biotechnologies, LLC (Tucson, Ariz.) as previously described[30]. Briefly, 10 mM stocks of inhibitors were diluted in DMSO to a concentration of 250 μM. Prior to initiating a profiling campaign, the compounds were evaluated for false positive against split-luciferase. The inhibitors were then each screened in duplicate against VEGFR-2. For kinase assays, each Cfluc-Kinase was translated along with Fos-Nfluc using a cell-free system (rabbit reticulocyte lysate) at 30° C. for 90 min. 24 μL aliquot of this lysate containing a kinase specific probe was added to 1 μL of either DMSO (for no-inhibitor control) or a 250 μM inhibitor solution in DMSO (final concentration of 10 μM) and incubated for 1 hour at room temperature. 80 μL of luciferin assay reagent was added to each solution and luminescence immediately measured on a luminometer. The % Inhibition was calculated using the following equation:

$$\% \text{ Inhibition} = \frac{ALU_{control} - ALU_{sample}}{ALU_{control}} \times 100$$

Immunoblotting.

Immunoblotting was performed as previously described.[19] Briefly, after appropriate treatments, the cells were washed with phosphate buffered saline (PBS) and lysed in lysis buffer. Cell lysates were immunoblotted. Membranes were blocked in 5% nonfat dry milk for one hour at room temperature and probed with appropriate antibodies. Membranes were then probed with horseradish peroxidase tagged anti-mouse or anti-rabbit IgG antibodies. Signal was detected using ECL solutions.

Reverse Transcriptase-PCR.

Total mRNA was collected and cDNA synthesized using a Qiagen RNeasykit (Valencia, Calif.) following manufacture's protocol. The PCR primers used are 5'-ACCATGTG-GACCTGTCACTGTCT-3' (p21 sense), 5'-AGAAGATG-TAGAGCGGGCCTITGA-3' (p21 antisense), 5'-ACGCA-TTTGGTCGTATTGGG-3' (GAPDH sense), and 5'-TGAT-TTTGGAGGGATCTCGC-3' (GAPDH antisense). Reverse-transcribed cDNA was subjected to 40 cycles. Thermal cycling conditions are as follows: denaturation for 30 seconds at 94° C. annealing for 30 seconds at 56.5° C. and elongation for 1 minute at 72° C. DNA was analyzed by 2% ethidium bromide agarose gel electrophoresis.

Cell Viability Assay.

TCA assay was conducted by NCI Developmental Therapeutics Program. Briefly, cells were plated in 96-well plates, and after appropriate treatments, the plates are incubated for an additional 48 h at 37° C., 5% $CO_2$. 95% air, and 100% relative humidity. The assay was terminated by the addition of cold TCA. Cells were fixed by the addition of 50 μl of cold 50% (w/v) TCA (final concentration, 10% TCA) and incubated for 60 minutes at 4° C. The plates were washed water and air dried. Sulforhodamine B (SRB) solution (100 μl) at 0.4% (w/v) in 1% acetic acid was added to each well, and plates were incubated for 10 minutes at room temperature. After staining, the plates were washed with 1% acetic acid and air dried. Bound stain was subsequently solubilized with 10 mM trizma base, and the absorbance was read on an automated plate reader at a wavelength of 515 nm.

Immunofluorescence.

After appropriate treatments in 8 well chamber slides. immunofluorescence was conducted as described previously.[19] Briefly, the cells were fixed in 2% paraformaldehyde and blocked in the blocking buffer. After blocking, the cells were incubated with appropriate antibody, incubated with anti-mouse or anti-rabbit IgG (H+L), F(ab')2 Fragment (Alexa Fluor® 488 Conjugate), and coverslipped with vectashield with DAPI. The specimens were examined by confocal microscopy.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating leukemia, the method comprising administering to a subject in need thereof a therapeutically effective amount of a chemotherapeutic agent and a therapeutically effective amount of a compound of Formula I:

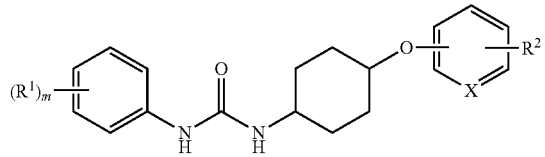

wherein
- $R^1$ is selected from the group consisting of halogen, $C_{1-6}$ haloalkyl and $C_{1-6}$ haloalkoxy;
- $R^2$ is selected from the group consisting of —CN, $C_{1-6}$ haloalkyl, $C_{1-6}$ haloalkoxy, —C(O)OR$^{2a}$ and —C(O)NR$^{2a}$R$^{2b}$;
- $R^{2a}$ and $R^{2b}$ are each independently selected from the group consisting of H, $C_{1-6}$ alkyl and $C_{3-8}$ cycloalkyl, or are taken together to form a 5- or 6-membered heterocycloalkyl ring;
- X is selected from the group consisting of —CH— and —N—; and
- subscript m is an integer from 1 to 3;
- such that when X is —CH—, $R^2$ is —C(O)OH, then subscript m is an integer 2 or 3;

and salts and isomers thereof;
thereby treating leukemia.

2. The method of claim 1, wherein said chemotherapeutic agent is selected from the group consisting of doxorubicin, cisplatinum, cyclophosphamide, chlorambucil and nitrogen mustard, and combinations thereof.

3. The method of claim 1, wherein said compound is selected from the group consisting of:

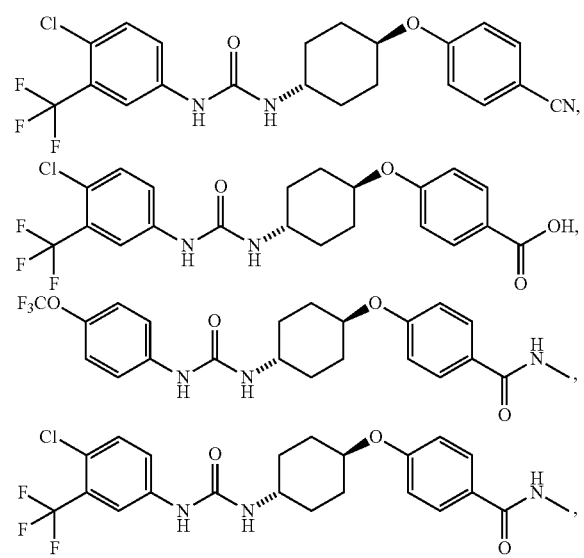

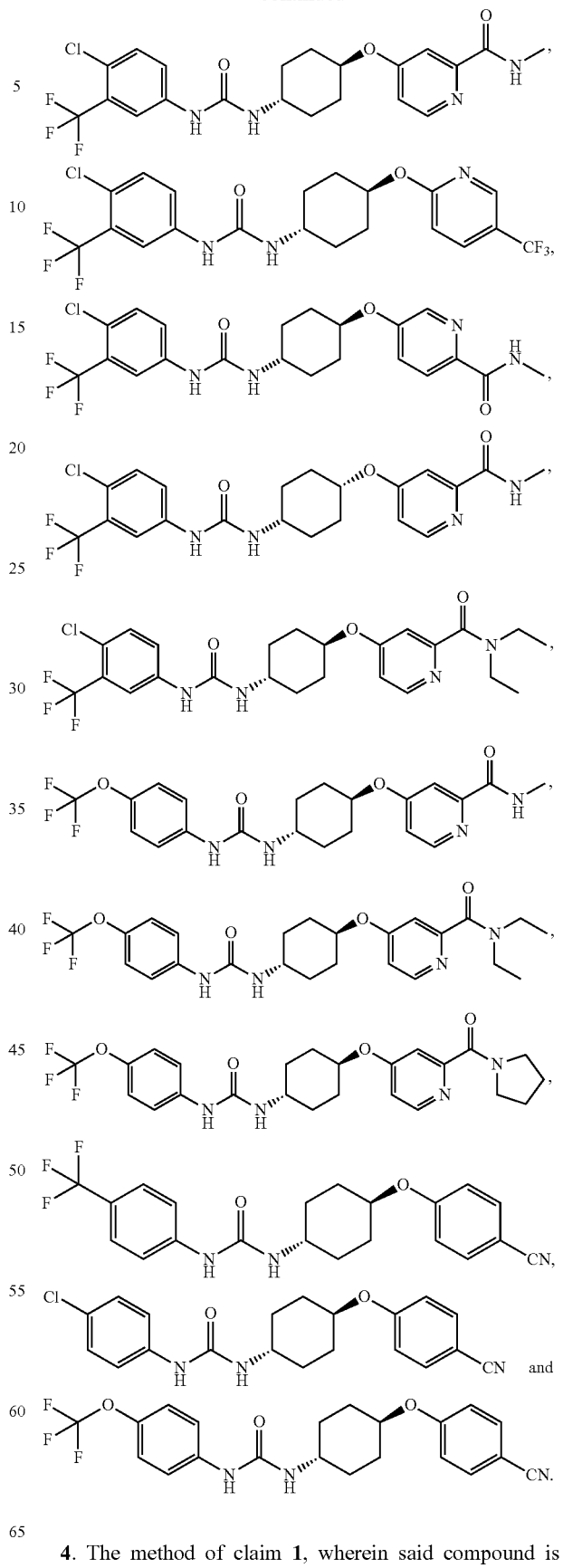

4. The method of claim 1, wherein said compound is selected from the group consisting of:

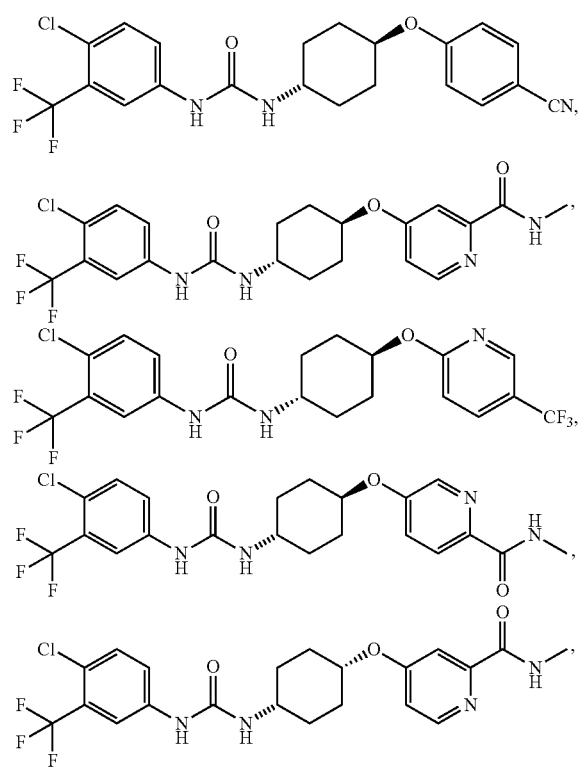
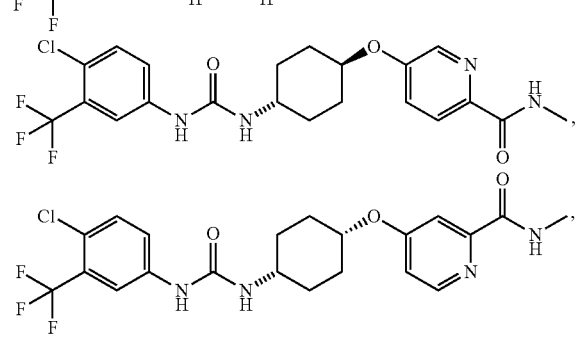
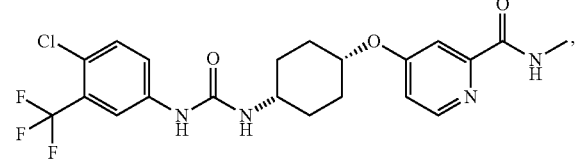
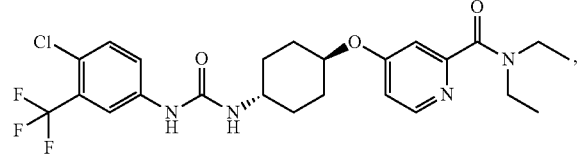
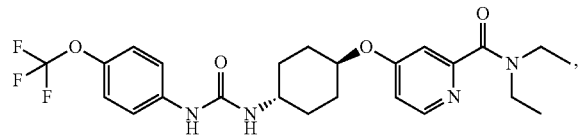
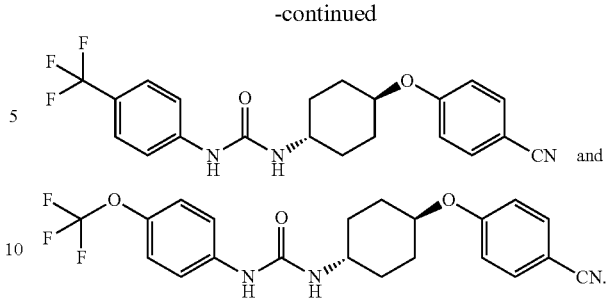
5. The method of claim 1, wherein said compound is selected from the group consisting of:
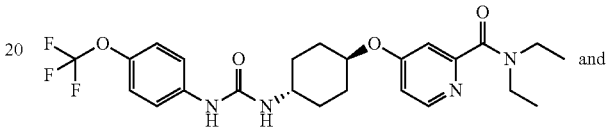
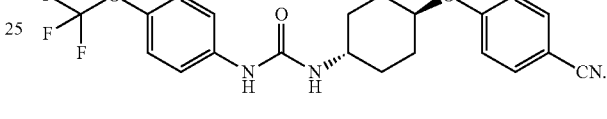
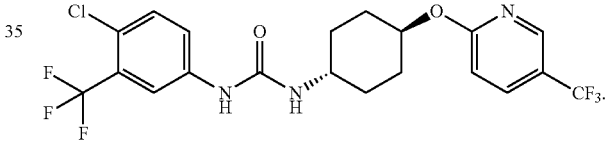
6. The method of claim 1, wherein said compound has the structure:
* * * * *